US009937183B2

(12) United States Patent
Kanyo et al.

(10) Patent No.: US 9,937,183 B2
(45) Date of Patent: *Apr. 10, 2018

(54) ANTIMICROBIAL COMPOUNDS AND METHODS OF MAKING AND USING THE SAME

(71) Applicant: Melinta Therapeutics, Inc., New Haven, CT (US)

(72) Inventors: Zoltan F. Kanyo, New Haven, CT (US); Ashoke Bhattacharjee, New Haven, CT (US)

(73) Assignee: Melinta Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/917,920

(22) PCT Filed: Sep. 9, 2014

(86) PCT No.: PCT/US2014/054860
§ 371 (c)(1),
(2) Date: Mar. 9, 2016

(87) PCT Pub. No.: WO2015/035421
PCT Pub. Date: Mar. 12, 2015

(65) Prior Publication Data
US 2016/0220568 A1 Aug. 4, 2016

Related U.S. Application Data

(60) Provisional application No. 61/875,642, filed on Sep. 9, 2013.

(51) Int. Cl.
*A61K 31/519* (2006.01)
*A01N 43/90* (2006.01)

(52) U.S. Cl.
CPC .................. *A61K 31/519* (2013.01)

(58) Field of Classification Search
CPC ..................... A61K 31/519; A01N 43/90
USPC ...................................... 514/265.1
See application file for complete search history.

(56) References Cited

U.S. PATENT DOCUMENTS

| | | | |
|---|---|---|---|
| 2,624,731 A | 1/1953 | Hitchings et al. |
| 3,980,781 A | 9/1976 | Snell et al. |
| 4,361,557 A | 11/1982 | Nagabhushan |
| 4,522,811 A | 6/1985 | Eppstein et al. |
| 4,971,965 A | 11/1990 | Ono et al. |
| 5,208,141 A | 5/1993 | Ikesu et al. |
| 5,434,257 A | 7/1995 | Matteucci et al. |
| 5,567,844 A | 10/1996 | Jommi et al. |
| 5,567,884 A | 10/1996 | Jommi et al. |
| 5,763,263 A | 6/1998 | Dehlinger |
| 5,763,588 A | 6/1998 | Matteucci et al. |
| 5,958,930 A | 9/1999 | Gangjee |
| 6,028,183 A | 2/2000 | Lin et al. |
| 6,110,925 A | 8/2000 | Williams et al. |
| 6,162,925 A | 12/2000 | Williams et al. |
| 6,617,332 B1 | 9/2003 | Brands et al. |
| 6,875,764 B1 | 4/2005 | Muzi et al. |
| 7,282,327 B2 | 10/2007 | McGall et al. |
| 9,023,843 B2 | 5/2015 | Duffy et al. |
| 9,193,731 B2 | 11/2015 | Duffy et al. |
| 9,216,979 B2 | 12/2015 | Duffy et al. |
| 9,221,827 B2 | 12/2015 | Duffy et al. |
| 2002/0016297 A1 | 2/2002 | Linde, II et al. |
| 2002/0193385 A1 | 12/2002 | Chambers et al. |
| 2003/0158403 A1 | 8/2003 | Manoharan et al. |
| 2005/0153992 A1 | 7/2005 | Tsutsumi et al. |
| 2006/0014743 A1 | 1/2006 | Boojamra et al. |
| 2006/0100224 A1 | 5/2006 | Svenstrup et al. |
| 2007/0206054 A1 | 9/2007 | Watanbe |
| 2008/0221095 A1 | 9/2008 | Gege et al. |
| 2008/0255164 A1 | 10/2008 | Albert et al. |
| 2010/0190747 A1 | 7/2010 | Suzuki et al. |
| 2010/0249126 A1 | 9/2010 | Burger et al. |
| 2016/0214988 A1 | 7/2016 | Kanyo et al. |

FOREIGN PATENT DOCUMENTS

| | | |
|---|---|---|
| CN | 1871240 | 11/2006 |
| CN | 101535311 | 9/2009 |
| DE | 10061537 | 6/2002 |
| DE | 10061538 | 6/2002 |
| DE | 10061541 | 6/2002 |

(Continued)

OTHER PUBLICATIONS

Corriere, M.D., et al, MRSA: An Evolving Pathogen: Disease-A-Month, vol. 54 pp. 751-755. Published 2008.*
Merriam-Webster: Definition of Prophylaxis.*
Aguilar et al., "Toward a library synthesis of the natural dipeptide antibiotic TAN 1057 A, B," Molecules. Jun. 30, 2002; 7(6):469-474.
Angelino et al., "On the oxidation of N-methyl and N-benzylpyrimidin-2-and-4-ones by rabbit liver aldehyde oxidase," Journal of heterocyclic chemistry. 1984; 21:749-752.
Ausin et al., "Synthesis of amino-and guanidino-G-clamp PNA monomers," Organic letters. Nov. 14, 2002; 4(23):4073-4075.
Babic et al., "What's new in antibiotic resistance? Focus on beta-lactamases," Drug resistance updates. Jun. 30, 2006; 9(3):142-156.

(Continued)

*Primary Examiner* — Timothy Thomas
*Assistant Examiner* — George W Kosturko
(74) *Attorney, Agent, or Firm* — Fish & Richardson P.C.

(57) ABSTRACT

Methods and compounds for treating, preventing, reducing the risk of and/or delaying the onset of a microbial infection in a subject are disclosed herein, wherein the microbial infection is caused by one or more microorganisms (e.g., one or more bacteria) which can be used as a biological weapon, such as *Bacillus anthracis, Franciscella tularensis, Yersinia pestis, Burkholderia mallei,* and *Burkholderia pseudomallei.* Also disclosed are pharmaceutical compositions or kits for treating, preventing, reducing the risk of and/or delaying the onset of a microbial infection.

11 Claims, 1 Drawing Sheet

(56) References Cited

FOREIGN PATENT DOCUMENTS

| | | |
|---|---|---|
| DE | 10061542 | 6/2002 |
| DE | 10133277 | 1/2003 |
| DE | 10141271 | 3/2003 |
| EP | 0339596 | 11/1989 |
| EP | 1113008 | 7/2001 |
| JP | S42025913 | 9/1965 |
| JP | 61091184 | 5/1986 |
| JP | 04077488 | 3/1992 |
| JP | H09506859 | 7/1997 |
| JP | H10503759 | 4/1998 |
| JP | 2001522369 | 11/2001 |
| JP | 2001522860 | 11/2001 |
| JP | 2004533406 | 11/2004 |
| JP | 2004537503 | 12/2004 |
| JP | 2005504020 | 2/2005 |
| JP | 2007270087 | 10/2007 |
| JP | 2008222557 | 9/2008 |
| JP | S5821681 | 10/2015 |
| KR | 20060118416 | 11/2006 |
| TW | 424090 | 3/2001 |
| TW | 99135283 | 10/2010 |
| TW | 201124417 | 7/2011 |
| WO | WO1994026722 | 11/1994 |
| WO | WO1995029894 | 11/1995 |
| WO | WO1997001562 | 1/1997 |
| WO | WO1998049177 | 11/1998 |
| WO | WO1999007685 | 2/1999 |
| WO | WO1999024452 | 5/1999 |
| WO | WO2000012484 | 3/2000 |
| WO | WO2001030749 | 5/2001 |
| WO | WO2001060825 | 8/2001 |
| WO | WO2002032920 | 4/2002 |
| WO | WO2002048138 | 6/2002 |
| WO | WO2002061110 | 8/2002 |
| WO | WO2002074773 | 9/2002 |
| WO | WO2002097134 | 12/2002 |
| WO | WO2003004602 | 1/2003 |
| WO | WO2003072574 | 9/2003 |
| WO | WO2004080466 | 9/2004 |
| WO | WO2005019228 | 3/2005 |
| WO | WO2005037801 | 4/2005 |
| WO | WO2007014308 | 2/2007 |
| WO | WO2007069923 | 6/2007 |
| WO | WO2007084786 | 7/2007 |
| WO | WO2008004796 | 1/2008 |
| WO | WO2008030119 | 3/2008 |
| WO | WO2008082440 | 7/2008 |
| WO | WO2008104279 | 9/2008 |
| WO | WO2008143729 | 11/2008 |
| WO | WO2008150406 | 12/2008 |
| WO | WO2008154642 | 12/2008 |
| WO | WO2009074812 | 6/2009 |
| WO | WO2009113828 | 9/2009 |
| WO | WO2011045415 | 4/2011 |
| WO | WO2011047319 | 4/2011 |
| WO | WO2012125832 | 9/2012 |
| WO | WO2012173689 | 12/2012 |
| WO | WO 2012173689 A2 * 12/2012 ........... C07D 487/04 | |
| WO | WO2015035421 | 3/2015 |
| WO | WO2015035426 | 3/2015 |

OTHER PUBLICATIONS

Bandow et al., "Proteomic approach to understanding antibiotic action," Antimicrobial agents and chemotherapy. Mar. 1, 2003; 47(3):948-955.
Banker et al, "Modern Pharmaceutices, 3ed.," Marcel Dekker, New York. 1996, pp. 451 and 596.
Bassetti et al., "New antibiotics for bad bugs: where are we," Ann Clin Microbiol Antimicrob. Aug. 28, 2013; 12(1):22.
Becker, "Antimicrobial drugs," Anesth Prog. 2013 Fall;60(3):111-122; quiz 123.

Belov et al., "First enantioselective synthesis of the novel antiinfective TAN-1057A via its aminomethyl-substituted dihydropyrimidinone heterocycle," Tetrahedron. Aug. 23, 2004; 60(35):7579-7589.
Berlinck, "Natural guanidine derivatives," Natural Product Reports. 1999; 16(3):339-365.
Böddeker et al., "Characterization of a novel antibacterial agent that inhibits bacterial translation," RNA. Sep. 1, 2002; 8(09):1120-1128.
Bondock et al., "Synthesis and antimicrobial activity of some new heterocycles incorporating antipyrine moiety," European journal of medicinal chemistry. Oct. 31, 2008; 43(10):2122-2129.
Brackmann et al., "Titanium-mediated cyclopropanation of N, N-dibenzylcarboxamides towards functionally substituted 2-(1'-aminocyclopropyl) acetic acids1," Synthesis. 2005(12):2008-2014.
Brands et al., "Dihydropyrimidinones—a new class of anti-Staphylococcal antibiotics," Bioorganic & medicinal chemistry letters. Jan. 20, 2003; 13(2):241-245.
Brands et al., "Novel antibiotics for the treatment of gram-positive bacterial infections," Journal of medicinal chemistry. Sep. 12, 2002; 45(19):4246-4253.
Brands et al., "Pyrimidinone antibiotics—heterocyclic analogues with improved antibacterial spectrum," Bioorganic & medicinal chemistry letters. Aug. 18, 2003; 13(16):2641-2645.
Budesinsky et al., Cesko-Slovenska Farmacie (1966), 15(8), 432-7; CA 67:90756, 1967. CAPLUS Abstract provided, 3 pages.
Buděsinský et al., "[5-Aryl-pyrimidines. 3. 5-Aryl-isocytosines and 5-aryl-4-thio-isocytosines]," Cesk Farm., 15(8):432-437, Oct. 1966.
Cahn and Ingold, "131. Specification of configuration about quadricovalent asymmetric atoms," Journal of the Chemical Society (Resumed). 1951:612-622.
Cahn et al., "Specification of Molecular Chirality" Angew. Chem. Int. Ed. Engl., 5(4):385-415, Apr. 1966.
Cahn et al., "The specification of asymmetric configuration in organic chemistry," Experientia. Mar. 1, 1965; 12(3):81-94.
Cahn. "An Introduction to the Sequence Rule: A System for the Specification of Absolute Configuration," J. Chem. Educ. 1964; 41(3):116-125.
CAS Registry No. 1056628-47-7, 1 page, Oct. 3, 2008.
CAS Registry No. 1056628-57-9, 2 pages, 2008.
CAS Registry No. 1056628-60-4, 2 pages, 2008.
CAS Registry No. 646521-61-1, 2 pages, 2003.
CAS Registry No. 646521-62-2, "(2R,4S,5R)-2-[2-(N-benzoylamino)-4-oxo-3,4-dihydropyrimidin-5-yl]-4-hydroxy-5-hydroxymethyl pyrrolidine," 3 pages, 2005.
CAS Registry No. 646521-63-3, "(2R,4S,5R)-N-[(9-fluorenylmethoxy)carbonyl]-2-[2-(N-benzoylamino)-4-oxo-3,4-dihydropyrimidin-5-yl]-4-hydroxy-5-hydroxymethyl pyrrolidine," 2 pages, 2005.
CAS Registry No. 646521-64-4, "(2R,4S,5R)-N-[(9-fluorenylmethoxy)carbonyl]-2[2-(N-benzoylamino)-4-oxo-3,4-dihydropyrimidin-5-yl]-5-[(4,4'-dimethoxy)triphenylmethyl]-oxymethyl-4-hydroxy pyrrolidine," 2 pages, 2005.
CAS Registry No. 646521-65-5, 2 pages, Feb. 5, 2004.
CAS Registry No. 667411-76-9, "2-benzoylamino-5-[2'-deoxy-3',5'-bis-O-(tert-butyldimethylsilyl)-β-D-erythro-pent-2-enofuranosyl]-3Hpyrimidin-4-one," 3 pages, 2003.
CAS Registry No. 667411-77-0, "N4-benzoyl-2'-deoxypseudoisocytidine," 3 pages, 2003.
CAS Registry No. 667411-78-1, 3 pages, 2003.
CAS Registry No. 667411-79-2, 1 page, Mar. 25, 2004.
CAS Registry No. 751437-20-4, 1 page, Sep. 24, 2004.
CAS Registry No. 646521-58-6, "(2R,5R)-N-(benzyloxy)carbonyl-2-[2-(N-benzoylamino)-4-oxo-3,4-dihydropyrimidin-5-yl]-4-[(tertbutyl)dimethylsilyl]oxy-5-[(tert-butyl)dimethylsilyl]oxymethyl-aza-cyclopent-3-ene," 3 pages, 2003.
Champney et al., "TAN-1057A: a translational inhibitor with a specific inhibitory effect on 50S ribosomal subunit formation," Current microbiology. Nov. 1, 2001; 43(5):340-345.
Chemical Abstracts Accession No. 1967:490756, 3 pages, 1966.
Chemical Abstracts Accession No. 2004:353887, 1 page, 2004.

(56) References Cited

OTHER PUBLICATIONS

Chou et al., "Quantitative analysis of dose-effect relationships: the combined effects of multiple drugs or enzyme inhibitors," Advances in enzyme regulation. Dec. 31, 1984; 22:27-55.
Chu et al., "Nucleosides XCII. A facile synthesis of 5-(β-d-ribofuranosyl)-isocytosine (ψ-isocytidine)," J Heterocycl Chem., Jan. 1, 1975;12(4):817-818.
Chu et al., Journal of Heterocyclic Chemistry (1975), 12(4), 817-18; CA 83:179473, 1975. CAPLUS Abstract provided, 3 pages.
Chu, "Acyclopyrimidine C-nucleosides. Synthesis of acyclopseudoisocytidine and its derivatives," J. Heterocyclic Chem., 21: 9-11, 1984.
Debaene et al., "Expanding the scope of PNA-encoded libraries: divergent synthesis of libraries targeting cysteine, serine and metallo-proteases as well as tyrosine phosphatases," Tetrahedron. Jul. 9, 2007; 63(28):6577-6586.
Dermer, "Another anniversary for the war on cancer," Nature Biotechnology. Mar. 1, 1994; 12(3):320.
Dyer et al., "Carbamates and Ureas Derived from Amino- and Oxopyrimidines," Journal of Organic Chemistry 27:982-985 (1962).
Fattori et al., "Drug-eluting stents in vascular intervention," The Lancet. Jan. 18, 2003; 361(9353):247-249.
Franceschi et al., "Structure-based drug design meets the ribosome," Biochemical pharmacology. Mar. 30, 2006; 71(7):1016-1025.
Freshney et al.,Culture of Animal Cells, A Manual of Basic Technique, Alan R. Liss, Inc., 1983, New York, p. 4.
Funabashi et al., "A new anti-MRSA dipeptide, TAN-1057 A," Tetrahedron. Jan. 1, 1993; 49(1):13-28.
Gangjee et al., "Synthesis of classical, three-carbon-bridged 5-substituted furo[2,3-d]pyrimidine and 6-substituted pyrrolo[2,3-d]pyrimidine analogues as antifolates," J Med Chem., 47(27):6893-6901, Dec. 30, 2004.
Gnad et al., "Synthesis and applications of β-aminocarboxylic acids containing a cyclopropane ring," Chemical reviews. Apr. 9, 2003; 103(4):1603-1624.
Gold et al., "Antimicrobial-drug resistance," New England Journal of Medicine. Nov. 7, 1996; 335(19):1445-1453.
Häberli et al., "Pyrrolidino-DNA," Nucleosides Nucleotides Nucleic Acids. May-Aug, 2003; 22(5-8):1187-1189.
Hershfield et al., "Antibacterial Activity of Novel RX-04 Compounds Against Biodefense Pathogens," Poster F-1522, 52nd ICAAC, 2012.
Housman et al., "In Vitro Evaluation of Rib-X Novel Compounds Against Selected Resistant Pseudomonas aeruginosa Isolates," Antimicrob. Agents Chemother., 05944, Dec. 27, 2011, 17 pages.
Hudson et al., "Fluorescent 7-deazapurine derivatives from 5-iodocytosine via a tandem cross-coupling-annulation reaction with terminal alkynes," Synlett. 2004(13):2400-2402.
Hudson et al., "Nucleobase modified peptide nucleic acid," Nucleosides, Nucleotides and Nucleic Acids. Oct. 1, 2003; 22(5-8):1029-1033.
Hudson et al., Canadian Journal of Chemistry, 86(11): 1026-1029, 2008.
Janeba et al., "Synthesis and Biological Evaluation of Acyclic 3-[(2-Hydroxyethoxy) methyl] Analogues of Antiviral Furo-and Pyrrolo [2, 3-d] pyrimidine Nucleosides 1," Journal of medicinal chemistry. Jul. 14, 2005; 48(14):4690-4696.
Katayama et al., "TAN-1057 AD, new antibiotics with potent antibacterial activity against methicillin-resistant Staphylococcus aureus. Taxonomy, fermentation and biological activity," The Journal of antibiotics. 1993; 46(4):606-613.
Kawahara et al., "Computer-Aided Molecular Design of Hydrogen Bond Equivalents of Nucleobases: Theoretical Study of Substituent Effects on the Hydrogen Bond Energies of Nucleobase Pairs," European Journal of Organic Chemistry. Jul. 1, 2003; 2003(14):2577-2584.
Kint et al., "New-found fundamentals of bacterial persistence," Trends in microbiology. Dec. 31, 2012;20(12):577-585.

Kordes et al., "Preparation of Cyclopropane Analogues of the Natural AntibioticTAN 1057 A/B," European journal of organic chemistry. Jul. 1, 2005; 2005(14):3008-3016.
Kosegi et al., JP 61091184; CA: 105:208920, 1986. CAPLUS Abstract provided.
Laufersweiler et al., "Synthesis and evaluation of tricyclic pyrrolopyrimidinones as dipeptide mimetics: Inhibition of interleukin-1β-converting enzyme," Bioorganic & medicinal chemistry letters. Oct. 1, 2005; 15(19):4322-4326.
Limburg et al., "Ribosomal alterations contribute to bacterial resistance against the dipeptide antibiotic TAN 1057," Antimicrobial agents and chemotherapy. Feb. 1, 2004; 48(2):619-622.
Lin et al., "Assembly of the TAN-1057 A/B heterocycle from a dehydroalanine precursor," Synthesis, 2000(14):2127-2130, 2000.
Lin et al., "Tricyclic 2'-deoxycytidine analogs: syntheses and incorporation into oligodeoxynucleotides which have enhanced binding to complementary RNA," Journal of the American Chemical Society. Apr. 1995; 117(13):3873-3874.
Liu et al., "Recent advances in the stereoselective synthesis of β-amino acids," Tetrahedron. Sep. 30, 2002; 58(40):7991-8035.
Lowy, "Antimicrobial resistance: the example of Staphylococcus aureus," Journal of Clinical Investigation. May 1, 2003;111(9):1265.
Lukin et al, "Rationalizing the strength of hydrogen-bonded complexes. Ab initio HF and DFT studies," The Journal of Physical Chemistry A. Jul. 25, 2002;106(29):6775-6782.
Magiorakos et al., "Multidrug-resistant, extensively drug-resistant and pandrug-resistant bacteria: an international expert proposal for interim standard definitions for acquired resistance," Clinical Microbiology and Infection. Mar. 1, 2012; 18(3):268-281.
Maguire, "Inhibition of bacterial ribosome assembly: a suitable drug target?" Microbiology and Molecular Biology Reviews. Mar. 1, 2009;73(1):22-35.
Matsuda et al., "Nucleosides. 120. Syntheses of 2'-deoxy-. psi.-isocytidine and 2'-deoxy-1-methyl-. psi.-uridine from. psi.-uridine," The Journal of Organic Chemistry. Aug. 1981;46(18):3603-3609.
Matsuda et al., Journal of Organic Chemistry (1981), 46(18), 3603-9; CA: 95:98205, 1981. CAPLUS Abstract provided.
Mayer et al., "Synthesis and triplex forming properties of pyrrolidino pseudoisocytidine containing oligodeoxynucleotides," Organic & biomolecular chemistry. 2005;3(9):1653-1658.
Mishra et al., "Dry Media Synthesis of Novel Pyrrolo-pyrimidines," Journal of Nepal Chemical Society. 2010; 25:83-88.
Miyaura et al., "A new stereospecific cross-coupling by the palladium-catalyzed reaction of 1-alkenylboranes with 1-alkenyl or 1-alkynyl halides," Tetrahedron Letters. Dec. 31, 1979; 20(36):3437-3440.
Moellering, "Linezolid: the first oxazolidinone antimicrobial," Annals of internal medicine. Jan. 21, 2003; 138(2):135-142.
Morice, "A new era in the treatment of coronary disease?" European heart journal. Feb. 1, 2003;24(3):209-211.
National Center for Biotechnology Information. PubChem Compound Database; CID=1112068, create date Jul. 10, 2005, 10 pages.
National Center for Biotechnology Information. PubChem Compound Database; CID=23522053, create date Dec. 6, 2007, 11 pages.
Nett, "The chemistry of gliding bacteria," Natural product reports. 2007; 24(6):1245-1261.
Orner et al., "The guanidinium group in molecular recognition: design and synthetic approaches," Journal of inclusion phenomena and macrocyclic chemistry. Dec. 1, 2001; 41(1-4):141-147.
Ortega et al., "Binding affinities of oligonucleotides and PNAs containing phenoxazine and G-clamp cytosine analogues are unusually sequence-dependent," Organic letters. Oct. 25, 2007; 9(22):4503-4506.
Paterson et al., "Extended-spectrum β-lactamases: a clinical update," Clinical microbiology reviews. Oct. 1, 2005;18(4):657-686.
Phillips, "Reactivity of 5-Bromoisocytosine with Some Amines," Journal of the American Chemical Society. Aug. 1953;75(16):4092.
Phillips, A. P., Journal of the American Chemical Society (1953), 75, 4092; CA 49:42634, 1955. CAPLUS Abstract provided, 1 page.

(56) References Cited

OTHER PUBLICATIONS

Pohl, "Zur Kenntnis des Dicyandiamids," [Investigations from the Organic Chemistry Laboratory of the Technical University of Dresden], Journal für Praktische Chemie., 77(1):533-548, May 14, 1908 [English machine translation], 30 pages.

Rajeev et al., "High-affinity peptide nucleic acid oligomers containing tricyclic cytosine analogues," Organic letters. Dec. 12, 2002; 4(25):4395-4398.

Ravin et al., "Preformulation," Remington's Pharm. Sci., Chapter 75, 1435-1450 (1990).

Rehm et al., "*Staphylococcus aureus*: methicillin-susceptible *S. aureus* to methicillin-resistant *S. aureus* and vancomycin-resistant *S. aureus*," Clinical Infectious Diseases. Sep. 15, 2010;51(Supplement 2):S176-S182.

Reigan et al., "Synthesis and enzymatic evaluation of xanthine oxidase-activated prodrugs based on inhibitors of thymidine phosphorylase," Bioorganic & medicinal chemistry letters. Nov. 1, 2004; 14(21):5247-5250.

Remington's Pharmaceutical Sciences, 18th ed. (Mack Publishing Company, 1990) Table of Contents p. xv, and chapter 75 pp. 1435-1450.

Rival et al., "Synthesis and antibacterial activity of some imidazo[1,2-a]pyrimidine derivatives," *Chem Pharm Bull* (Tokyo)., 40(5):1170-1176, May 1992.

Šála et al., "Synthesis of racemic 2-hydroxy-4-and 2-hydroxy-5-(hydroxymethyl) cyclohexane pyrimidine C-nucleoside analogues," Collection of Czechoslovak chemical communications, 69(4): 918-932, 2004.

Sala et al., Collection of Czechoslovak Chemical Communications (2004), 69(4), Abstract provided. 918-932; CA: 141:314551, 2004. CAPLUS Abstract provided, 3 pages.

Samir Bondock et al., "Synthesis and antimicrobial activity of some new heterocycles incorporating antipyrine moiety", European Journal of Medicinal Chemistry, 43:10, Oct. 1, 2008, pp. 2022-21229, XP055132947.

Sanders et al., "Disease-related misassembly of membrane proteins," Annu. Rev. Biophys. Biomol. Struct. Jun. 9, 2004; 33:25-51.

Sato et al., "A stereocontrolled synthesis of C-4' alkylated pyrimidine C-nucleosides," Tetrahedron Letters. Dec. 31, 1979;20(31):2897-2900.

Sato et al., "A Convenient Route to 5'-Modified Pseudoisocytidines and 2-Thiopseudouridines," Chemistry Letters. 1978; 7(11):1297-1300.

Sato et al., Chemistry Letters (1978), (11), 1297-300; CA 90:87793, 1979. CAPLUS Abstract provided, 4 pages.

Sato et al., Tetrahedron Letters (1979), (31), 2897-900; CA 92:164211, 1980. CAPLUS Abstract provided, 2 pages.

Shaffer, "The challenge of antibiotic-resistant *Staphylococcus*: lessons from hospital nurseries in the mid-20th century," The Yale journal of biology and medicine. Jun. 2013; 86(2):261.

Singh, "Confronting the challenges of discovery of novel antibacterial agents," Bioorganic & medicinal chemistry letters. Aug. 15, 2014; 24(16):3683-3689.

Sniady et al., "Zinc-catalyzed cycloisomerizations. Synthesis of substituted furans and furopyrimidine nucleosides," The Journal of organic chemistry. Jul. 3, 2008; 73(15):5881-5889.

Sokolov et al., "Total Synthesis of TAN-1057 A/B, a New Dipeptide Antibiotic from *Flexibacter* sp. PK-74," European journal of organic chemistry. May 1, 1998; 1998(5):777-783.

Stoss et al., "Novel pyrimidine and pyrimido[1, 2-a]pyrimidine derivatives. By-products of a guanidine based thymine synthesis," Journal of Heterocyclic Chemistry, 28(2):231-236, Feb./Mar. 1991.

Theuretzbacher et al., "Update on antibacterial and antifungal drugs—can we master the resistance crisis?" Current opinion in pharmacology. Oct. 31, 2011; 11(5):429-432.

Toutouzas et al., "Sirolimus-eluting stents: a review of experimental and clinical findings," Zeitschrift für Kardiologie. Jul. 1, 2002; 91(3):49-57.

Tsiodras et al., "Linezolid resistance in a clinical isolate of *Staphylococcus aureus*," The Lancet. Jul. 21, 2001;358(9277):207-8.

Wang et al., "A highly enantioselective hetero-Diels-Alder reaction of aldehydes with Danishefsky's diene catalyzed by chiral titanium (IV) 5, 5', 6, 6', 7, 7', 8, 8'-octahydro-1, 1'-bi-2-naphthol complexes," The Journal of organic chemistry. Apr. 5, 2002;67(7):2175-2182.

Wang, Tw 424090; CA: 138:205080, 2003. CAPLUS Abstract provided, 1 page.

Williams et al., "Synthesis and antimicrobial evaluation of TAN-1057A/B analogs," The Journal of antibiotics. 1998; 51(2):189-201.

Wilson, "The A-Z of bacterial translation inhibitors. Critical Reviews in Biochemistry and Molecular Biology," Dec. 1, 2009; 44(6):393-433.

Wojciechowski et al., "Exceptional Fluorescence and Hybridization Properties of a Phenylpyrrolocytosine in Peptide Nucleic Acid," InNucleic Acids Symposium Series Sep. 1, 2008 (vol. 52, No. 1, pp. 401-402). Oxford University Press.

Wojciechowski et al., "Peptide nucleic acid containing a meta-substituted phenylpyrrolocytosine exhibits a fluorescence response and increased binding affinity toward RNA," Organic letters. Sep. 29, 2009; 11(21):4878-4881.

Wojciechowski, "Fluorescence and hybridization properties of peptide nucleic acid containing a substituted phenylpyrrolocytosine designed to engage guanine with an additional H-bond," Journal of the American Chemical Society. Aug. 30, 2008; 130(38):12574-12575.

Wolff Manfred E. "Burger's Medicinal Chemistry, 5ed, Part 1", John Wiley & Sons, 1995, pp. 975-977.

Xu et al., "A new and convergent synthesis for 2, 5-diamino-tetrahydropyrimidones," Tetrahedron letters. Mar. 17, 2003; 44(12):2601-2604.

Xu et al., "SAR studies on dihydropyrimidinone antibiotics," Bioorganic & medicinal chemistry letters. Mar. 15, 2011; 21(6):1670-1674.

Yuan et al., "Total synthesis of the anti methicillin-resistant *Staphylococcus aureus* peptide antibiotics TAN-1057A-D," Journal of the American Chemical Society. Dec. 10, 1997; 119(49):11777-11784.

Zhang et al., "A facile construction of the 3, 6-diamino-1, 2, 3, 4-tetrahydropyridine-4-one scaffold: synthesis of N-3 to carbon replacement analog of TAN-1057A/B," Tetrahedron letters. Apr. 30, 2007; 48(18):3273-3275.

Zhang et al., "A new approach to the 2, 5-diamino-5, 6-dihydro-1H-pyrimidine-4-one derivatives: synthesis of TAN-1057A/B and analogs," Tetrahedron letters. Jul. 28, 2003; 44(31):5871-5873.

Zhou et al., "Design at the atomic level: design of biaryloxazolidinones as potent orally active antibiotics," Bioorg Med Chem Lett., 18(23):6175-6178, Epub Oct. 7, 2008.

Zhou et al., "Design at the atomic level: generation of novel hybrid biaryloxazolidinones as promising new antibiotics," Bioorg Med Chem Lett., 18(23):6179-6183, Epub Oct. 7, 2008.

Zlatko Janeba., "Synthesis and Biological Evaluation of Acyclic 3-[(2-Hydroxyethoxy) methyl] Analogues of Antiviral Furo- and Pyrrolo [2,3-d] pyrimidine Nucleosides". J Med Chem, Jul. 14, 2005; 14:48(14): 4690-6.

Antimicrobial Agents and Chemotherapy 2012, p. 1646-1649.

Anonymous: "U.S. Government Lists of 1-12 Bioterrorism Agents and Diseases", Biosecurity and Biodefense Resource, Jan. 1, 2007 (Jan. 1, 2007), XP055352854, Retrieved from the Internet:URL:https://fas. org/biosecurity/resource/lists.htm [retrieved on Mar. 8, 2017].

Biochemistry. 2009, 48, pp. 7547-7555.

Biopolymers and Cell, 2009, 25(6), pp. 491-499.

Extended European Search Report for Application No. 14841546.6, dated Apr. 28, 2017, 10 pages.

International Preliminary Report on Patentability for PCT/US2014/054860, dated Mar. 24, 2016, 9 pages.

Indian Journal of Chemistry, Section B: Organic Chemistry Including Medicinal Chemistry, 1992, 31B(2), pp. 105-108.

JACS, 2009, 131(12), pp. 4288-4293.

Tawain Office Action in Japanese Application No. 104131806, dated Jul. 4, 2017, 56 pages.

Japanese Office Action in Japanese Application No. 2016-37911, dated Feb. 7, 2017, 17 pages.

Mikrobiologichnii Zhurnal 2010, 72(2), pp. 36-42.

(56) References Cited

OTHER PUBLICATIONS

PNAS, 2006, 103(17), pp. 6665-6669.
Supplementary European Search Report in European Application No. EP14841940, dated Mar. 8, 2017, 5 pages.

* cited by examiner

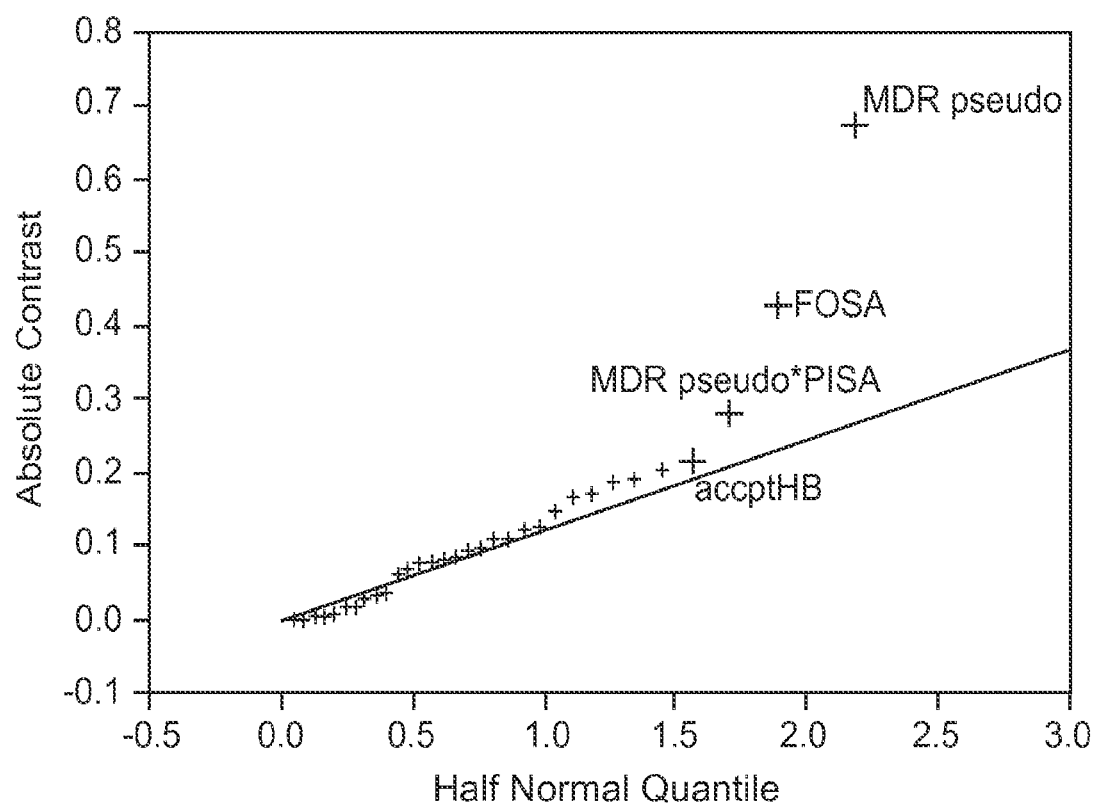

ANTIMICROBIAL COMPOUNDS AND METHODS OF MAKING AND USING THE SAME

RELATED APPLICATIONS

This application is a U.S. national stage under 35 U.S.C. § 371 of International Application No. PCT/US2014/054860, filed on Sep. 9, 2014, which claims priority to, and the benefit of, U.S. Provisional Application No. 61/875,642, filed Sep. 9, 2013, the entire contents of which are incorporated herein by reference in their entireties.

GOVERNMENT SUPPORT

This invention was made with U.S. Government support under Defense Threat Reduction Agency (DTRA), Project 922141, MRMC Control Number W81XWH-12-0162. The Government has certain rights in the invention.

BACKGROUND OF THE INVENTION

Biological agents, including various types of bacteria such as *Bacillus anthracis* and Multi Drug Resistant (MDR) *anthracis*, *Franciscella tularensis*, *Yersinia pestis*, *Burkholderia mallei*, *Burkholderia pseudomallei*, and other category A or B biodefense pathogens, can be used as weapons, which pose a material threat to the national security and public health in the United States.

Therefore, there is a need for effective anti-bacterial agents for the prevention, prophylaxis, and treatment of infections caused by biological agents, including those that can be used as weapons.

SUMMARY OF THE INVENTION

In one aspect, the invention pertains, at least in part, to a method of treating, preventing, reducing the risk of, or delaying the onset of a microbial infection in a subject, comprising administering to the subject an effective amount of a compound selected from Compounds 1-17, having the following structures:

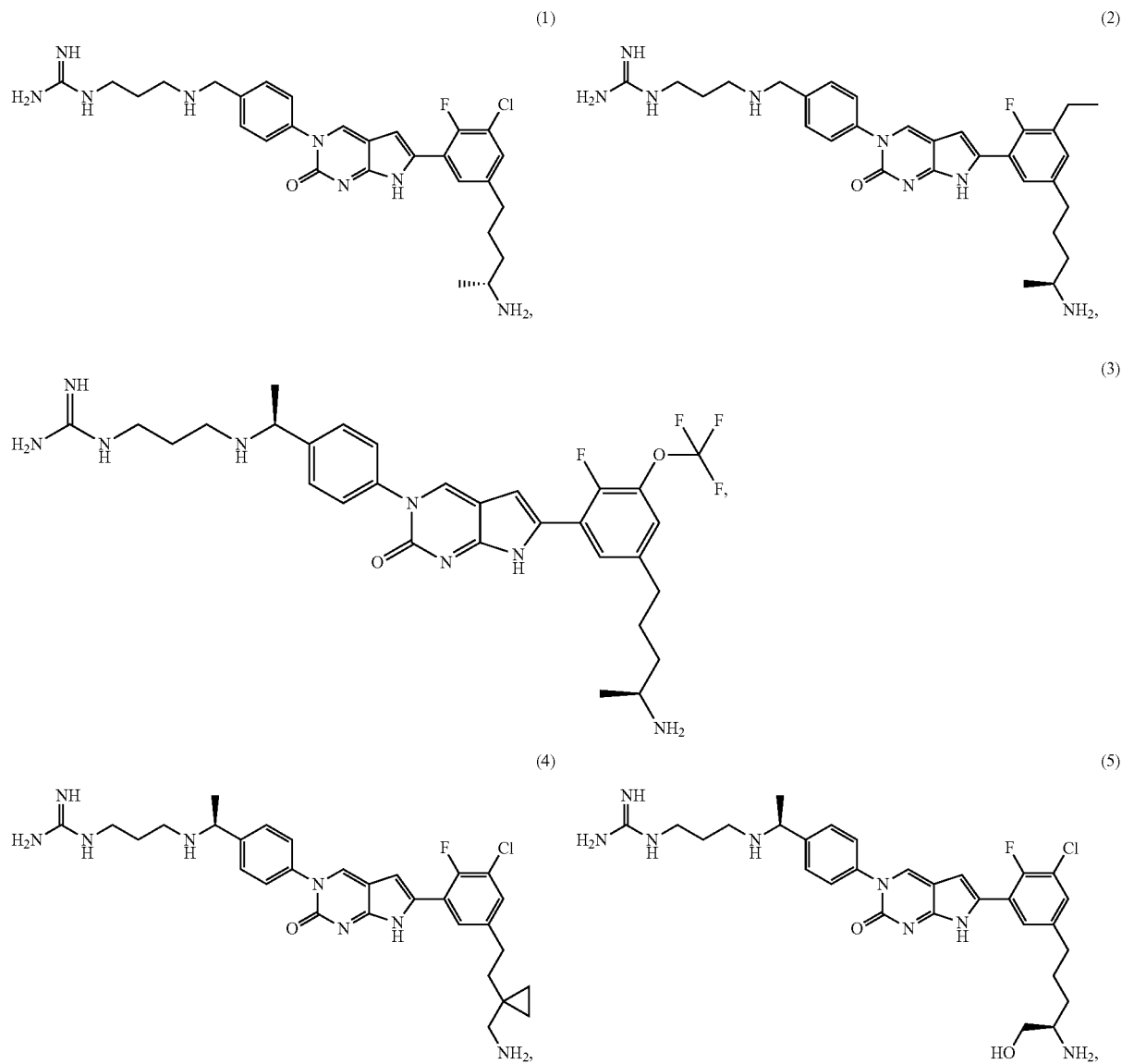

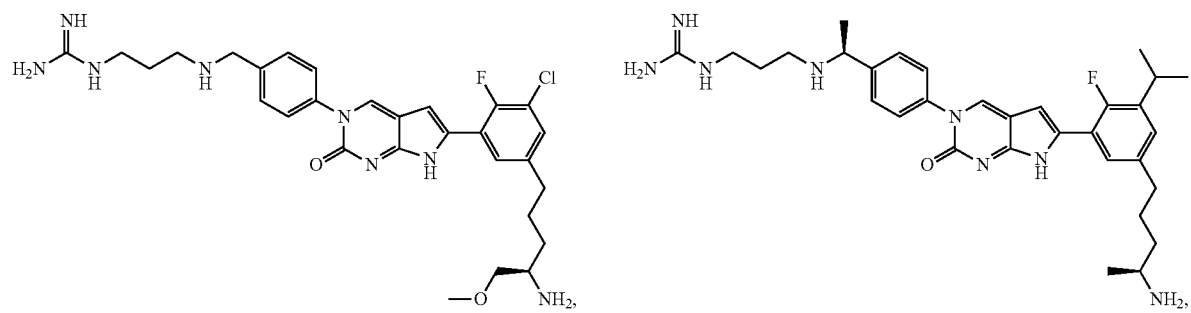
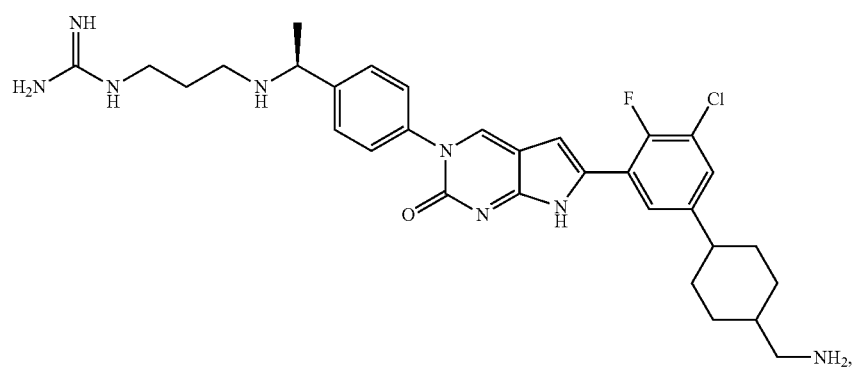
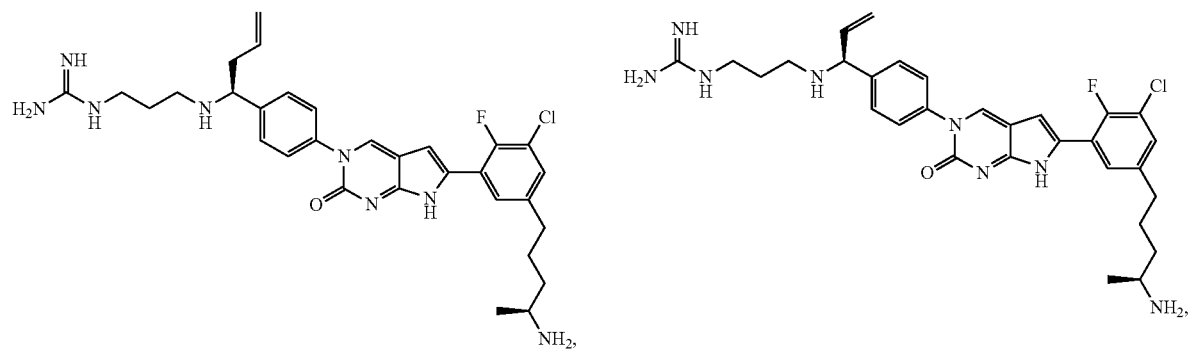
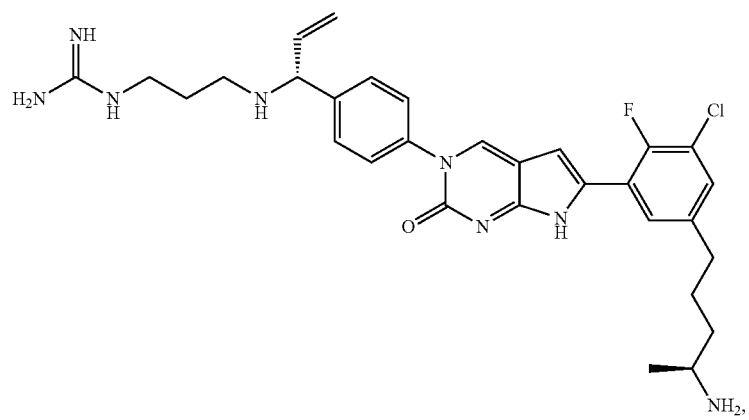

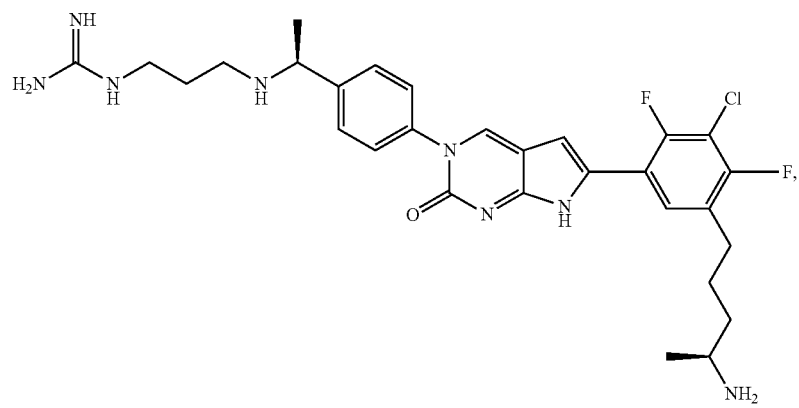
(12)
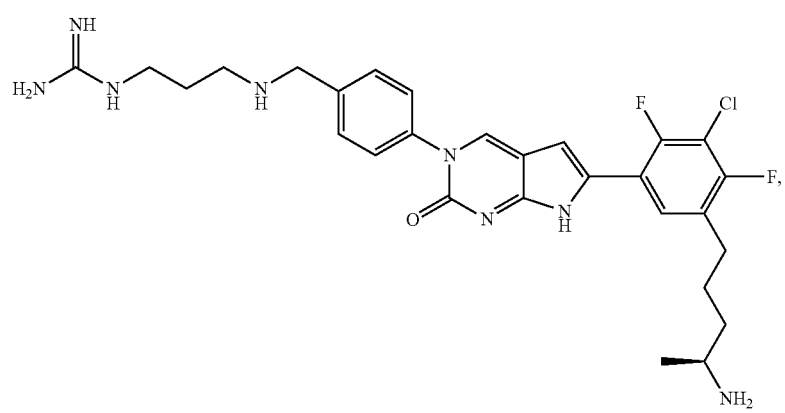
(13)
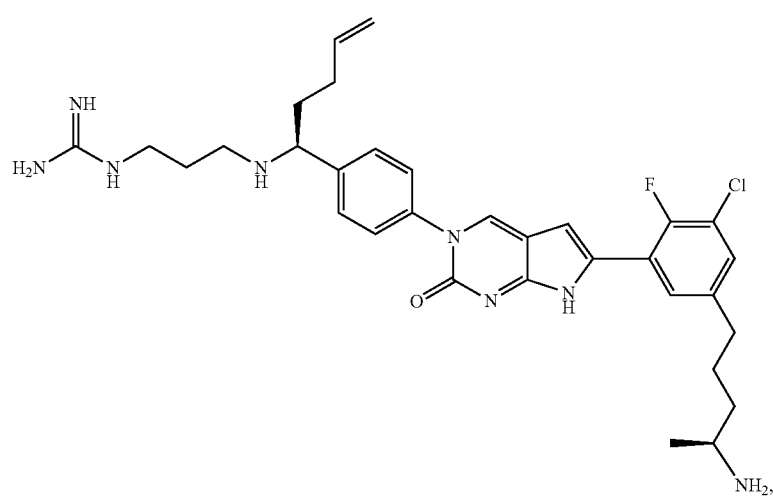
(14)

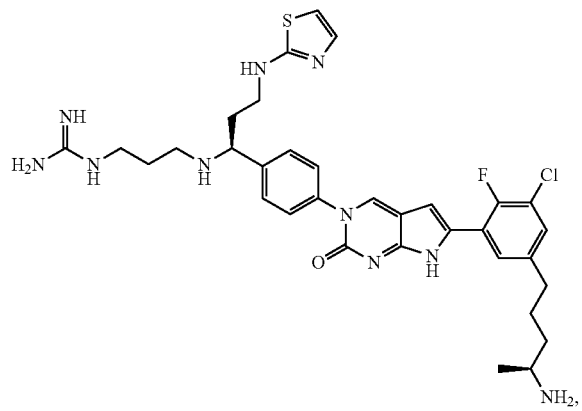

(15)

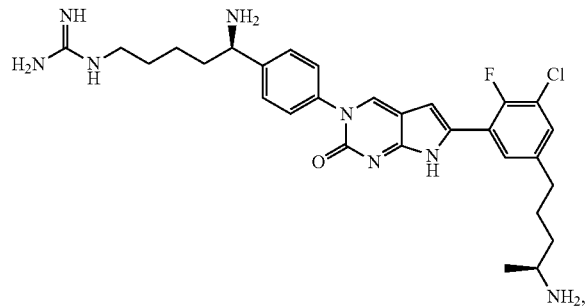

(16)

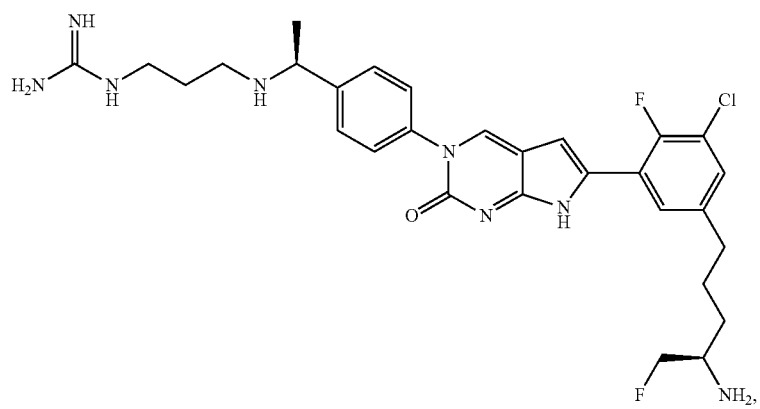

(17)

stereoisomers, tautomers, and salts thereof, wherein the infection is caused by or involves one or more microorganisms which are capable of being used as biological weapons, or the infection is caused by or involves one or more microorganisms which are extremely-drug resistant Gram-positive or Gram-negative pathogens.

In a second aspect, the invention relates to a kit for use in treating, preventing, reducing the risk of or delaying the onset of a microbial infection in a subject. The kit includes a container, a compound selected from Compounds 1-17 and stereoisomers, tautomers, and salts thereof, and instructions for use in the treatment, prevention, or reduction of the risk of a microbial infection that is caused by or involves one or more microorganisms which are capable of being used as biological weapons, or the infection is caused by or involves one or more microorganisms which are extremely-drug resistant Gram-positive or Gram-negative pathogens.

A third aspect of the invention relates to a compound for use in the manufacture of a medicament for treating a microbial infection in a subject, wherein the compound is selected from Compounds 1-17 and stereoisomers, tautomers, and salts thereof, and wherein the infection is caused by or involves one or more microorganisms which are capable of being used as biological weapons, or the infection is caused by or involves one or more microorganisms which are extremely-drug resistant Gram-positive or Gram-negative pathogens.

A fourth aspect of the invention relates to a compound for use in the manufacture of a medicament for preventing a microbial infection in a subject, wherein the compound is selected from Compounds 1-17 and stereoisomers, tautomers, and salts thereof, and wherein the infection is caused by or involves one or more microorganisms which are capable of being used as biological weapons, or the infection is caused by or involves one or more microorganisms which are extremely-drug resistant Gram-positive or Gram-negative pathogens.

A fifth aspect of the invention relates to a compound for use in the manufacture of a medicament for reducing the risk of a microbial infection in a subject, wherein the compound is selected from Compounds 1-17 and stereoisomers, tautomers, and salts thereof, and wherein the infection is caused by or involves one or more microorganisms which are capable of being used as biological weapons, or the infection is caused by or involves one or more microorganisms which are extremely-drug resistant Gram-positive or Gram-negative pathogens.

A sixth aspect of the invention relates to a compound for use in the manufacture of a medicament for delaying the onset of a microbial infection in a subject, wherein the compound is selected from Compounds 1-17 and stereoisomers, tautomers, and salts thereof, and wherein the infection is caused by or involves one or more microorganisms which are capable of being used as biological weapons, or the infection is caused by or involves one or more microorganisms which are extremely-drug resistant Gram-positive or Gram-negative pathogens.

In a seventh aspect, the invention relates to a compound for use in a method of treating, preventing, reducing the risk of, and/or delaying the onset of a microbial infection in a subject, wherein the compound is selected from Compounds 1-17 and stereoisomers, tautomers, and salts thereof, and wherein the infection is caused by or involves one or more microorganisms which are capable of being used as biological weapons, or the infection is caused by or involves one or more microorganisms which are extremely-drug resistant Gram-positive or Gram-negative pathogens.

DESCRIPTION OF THE FIGURES

FIG. 1 is a half-normal plot from a sensitivity analysis on effects driving the antibacterial activity, with emphasis on the activity against *B. pseudomallei*.

DETAILED DESCRIPTION OF THE INVENTION

The invention is based, at least in part, on an unexpected discovery that certain pyrrolocytosine compounds are effective for treating, preventing, reducing the risk of, and/or delaying the onset of infections caused by various types of microorganisms (e.g., bacteria) that can be used as biological weapons.

In some embodiments, the present invention relates to a method of treating, preventing, reducing the risk of, or delaying the onset of a disease state in a human or animal comprising administering to the human or animal in need thereof an effective amount of one or more compounds selected from Compounds 1-17 disclosed herein, including stereoisomers, tautomers, and salts thereof.

In one embodiment, the invention pertains, at least in part, to a method of treating, preventing, or reducing the risk of, or delaying the onset of a microbial, e.g., bacterial, infection in a subject, comprising administering to the subject an effective amount of one or more compounds selected from Compounds 1-17 disclosed herein, including stereoisomers, tautomers, and salts thereof, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In some embodiments, the present invention relates to use of one or more compounds selected from Compounds 1-17 disclosed herein, including stereoisomers, tautomers, and salts thereof, in the manufacture of a medicament for treating, preventing, reducing the risk of, or delaying the onset of a microbial infection in a human or animal, wherein the infection is caused by or involves one or more microorganisms which are capable of being used as biological weapons.

In some embodiments, the present invention relates to one or more compounds selected from Compounds 1-17 disclosed herein, including stereoisomers, tautomers, and salts thereof, for use in treating, preventing, reducing the risk of, or delaying the onset of a microbial infection in a human or animal, wherein the infection is caused by or involves one or more microorganisms which are capable of being used as biological weapons.

In one embodiment, the invention pertains, at least in part, to a method of treating, preventing, reducing the risk of, or delaying the onset of a microbial, e.g., bacterial, infection in a subject, comprising administering to the subject an effective amount of one or more compounds selected from Compounds 1-17 disclosed herein, including stereoisomers, tautomers, and salts thereof, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In one embodiment, the invention pertains, at least in part, to a method of treating a microbial, e.g., bacterial, infection in a subject, comprising administering to the subject an effective amount of one or more compounds selected from Compounds 1-17 disclosed herein, including stereoisomers, tautomers, and salts thereof, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In one embodiment, the invention pertains, at least in part, to a method of preventing a microbial, e.g., bacterial, infection in a subject, comprising administering to the subject an effective amount of one or more compounds selected from Compounds 1-17 disclosed herein, including stereoisomers, tautomers, and salts thereof, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In another embodiment, the invention pertains, at least in part, to a method of reducing the risk of a microbial, e.g., bacterial, infection in a subject, comprising administering to the subject an effective amount of one or more compounds selected from Compounds 1-17 disclosed herein, including stereoisomers, tautomers, and salts thereof wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In another embodiment, the invention pertains, at least in part, to a method of delaying the onset of a microbial, e.g., bacterial, infection in a subject, comprising administering to the subject an effective amount of one or more compounds selected from Compounds 1-17 disclosed herein, including stereoisomers, tautomers, and salts thereof, wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In another embodiment, the invention pertains, at least in part, to a compound for use in the manufacture of a medicament for treating a microbial, e.g., bacterial, infection in a subject, wherein the compound is selected from Compounds 1-17 and stereoisomers, tautomers, and salts thereof, and wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In another embodiment, the invention pertains, at least in part, to a compound for use in the manufacture of a medicament for preventing a microbial, e.g., bacterial, infection in a subject, wherein the compound is selected from Compounds 1-17 and stereoisomers, tautomers, and salts thereof, and wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In another embodiment, the invention pertains, at least in part, to a compound for use in the manufacture of a medicament for reducing the risk of a microbial, e.g., bacterial, infection in a subject, wherein the compound is selected from Compounds 1-17 and stereoisomers, tautomers, and salts thereof, and wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In yet another embodiment, the invention pertains, at least in part, to a compound for use in the manufacture of a medicament for delaying the onset of a microbial, e.g., bacterial, infection in a subject, wherein the compound is selected from Compounds 1-17 and stereoisomers, tautomers, and salts thereof, and wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In yet another embodiment, the invention pertains, at least in part, to a compound, or a pharmaceutical composition thereof, for use in a method of treating, preventing, reducing the risk of, and/or delaying the onset of a microbial, e.g., bacterial, infection in a subject, wherein the compound is selected from Compounds 1-17 and stereoisomers, tautomers, and salts thereof, and wherein the infection is caused by or involves one or more microorganisms which are capable of being used as biological weapons, e.g., wherein the one or more microorganisms are selected from *Bacillus anthracis* and Multi Drug Resistant (MDR) *anthracis, Franciscella tularensis, Yersinia pestis, Burkholderia mallei*, and *Burkholderia pseudomallei*.

In a particular embodiment, the invention pertains, at least in part, to a method of treating an infection in a subject, preventing an infection in a subject, reducing the risk of an infection in a subject, or delaying the onset of an infection in a subject comprising administering to the subject an effective amount of one or more compounds selected from Compounds 14-17 disclosed herein, including stereoisomers, tautomers, and salts thereof, wherein the infection is caused by a *bacterium* which can be used as a biological weapon.

In one embodiment, the present invention relates to, at least in apart, a kit comprising a container, a compound selected from Compounds 1-17 and stereoisomers, tautomers, and salts thereof, and instructions for use in the treatment of a microbial infection that is caused by or involves one or more microorganisms, e.g., biodefense category A pathogens or biodefense category B pathogens, which are capable of being used as biological weapons. In one embodiment, the one or more microorganisms are selected from *Bacillus anthracis, Franciscella tularensis, Yersinia pestis, Burkholderia mallei*, and *Burkholderia pseudomallei*.

In another embodiment, the present invention relates to, at least in a part, to a kit comprising a container, a compound selected from Compounds 1-17 and stereoisomers, tautomers, and salts thereof, and instructions for use in the prevention of a microbial infection that is caused by or involves one or more microorganisms, e.g., biodefense category A pathogens or biodefense category B, pathogens, which are capable of being used as biological weapons. In one embodiment, the one or more microorganisms are selected from *Bacillus anthracis, Franciscella tularensis, Yersinia pestis, Burkholderia mallei*, and *Burkholderia pseudomallei*.

In yet another embodiment, the present invention relates to, at least in a part, to a kit comprising a container, a compound selected from Compounds 1-17 and stereoisomers, tautomers, and salts thereof, and instructions for use in reducing the risk of a microbial infection that is caused by or involves one or more microorganisms, e.g., biodefense category A pathogens or biodefense category B, which are capable of being used as biological weapons. In one embodiment, the one or more microorganisms are selected from *Bacillus anthracis, Franciscella tularensis, Yersinia pestis, Burkholderia mallei*, and *Burkholderia pseudomallei*.

In another embodiment, the present invention relates to, at least in a part, to a kit comprising a container, a compound selected from Compounds 1-17 and stereoisomers, tautomers, and salts thereof, and instructions for use in delaying the onset of a microbial infection that is caused by or involves one or more microorganisms, e.g., biodefense category A pathogens or biodefense category B, which are capable of being used as biological weapons. In one embodiment, the one or more microorganisms are selected from *Bacillus anthracis, Franciscella tularensis, Yersinia pestis, Burkholderia mallei*, and *Burkholderia pseudomallei*.

In embodiments, the one or more microorganisms are biodefense category A or B pathogens. Category A pathogens are those organisms/biological agents that pose the highest risk to national security and public health because they (1) can be easily disseminated or transmitted from person to person, (2) result in high mortality rates and have the potential for major public health impact, (3) might cause public panic and social disruption, and (4) require special action for public health preparedness. Examples of category A pathogens include but are not limited to *Bacillus anthracis, Franciscella tularensis, Yersinia pestis*, Ebola, Marburg, Ebola-like viruses such as *Bundibugyo ebolavirus, Sudan ebolavirus, Tai Forest ebolavirus, Zaire ebolavirus* and Marburg-like viruses such as Marburg virus and Ravn virus. Category B pathogens are the second highest priority organisms/biological agents. They are moderately easy to disseminate, result in moderate morbidity rates and low mortality rates, and require specific enhancements for diagnostic capacity and enhanced disease surveillance. Examples of category B pathogens include but are not limited to *Burkholderia pseudomallei, Staphylococcus enterotoxin* B, and Hepatitis A.

More examples of category A or B pathogens are provided by the National Institute of Allergy and Infectious Diseases (NIAID), including category A pathogens *Bacillus anthracis* (anthrax), *Yersinia pestis* (plague), and *Fracisella tularensis* (tularemia), and category B pathogens *Burkholderia pseudomallei, Coxiella burnetii* (Q fever), *Brucella* species (brucellosis), *Burkhoderia mallei* (glanders), *Chlamydia psittaci* (Psittacosis), Typhus fever (*Rickettsia prowazekii*), and Food- and Waterborne Bacterial pathogens: Diarrheagenic *E. coli*, Pathogenic Vibrios, *Shigella* species, *Salmonella, Listeria monocytogenes, Campylobacter jejuni*, and *Yersinia enterocolitica*.

In one embodiment, the compound used for the method of the invention is selected from the group consisting of Compounds 14-17, stereoisomers, tautomers, and salts thereof, and the one or more microorganisms are selected from *Bacillus anthracis, Franciscella tularensis, Yersinia pestis, Burkholderia mallei,* and *Burkholderia pseudomallei.*

In one embodiment, the one or more microorganisms are extremely-drug resistant Gram-positive or Gram-negative pathogens.

In one embodiment, the compound used for the method of the invention is selected from the group consisting of Compounds 1-13, stereoisomers, tautomers, and salts thereof, and the one or more microorganisms are selected from *Burkholderia mallei* and *Burkholderia pseudomallei.*

In embodiments, the salts of the compounds described herein are pharmaceutically acceptable salts. For example, the salts of the compounds described herein (e.g., Compounds 14-17) are hydrochloride salts.

In one embodiment, a *bacterium* which can be used as a biological weapon includes a *bacterium* which possesses one or more of the characteristics, including but not limited to, easily being produced or disseminated, easily being transmitted from person to person, having potential or moderate or high morbidity, having potential for moderate or high mortality, having potential for causing public panic and social disruption, requiring special action for public health preparedness, and requiring specific enhancements for diagnosis and disease surveillance.

In another embodiment, a *bacterium* which can be used as a biological weapon is stable or viable (e.g., capable of performing all or part of its normal biological functions, such as replicating, forming spores, and infecting a subject) under various conditions (e.g., heat, cold, high pressure, low pressure, acidic or basic conditions, humidity, dryness, and radiation), including extreme conditions. In one embodiment, a *bacterium* which can be used as a biological weapon is capable of infecting a subject under various conditions. In one embodiment, a *bacterium* which can be used as a biological weapon is stable or viable at a temperature above 25° C., 30° C., 40° C., 50° C., 60° C., 70° C., 80° C., 90° C., 100° C., 125° C., 150° C., 175° C., or 200° C. In another embodiment, a *bacterium* which can be used as a biological weapon is stable or viable at a temperature below 25° C., 20° C., 10° C., 5° C., 0° C., -10° C., -20° C., -30° C., -40° C., -50° C., -60° C., -70° C., -100° C. or -150° C. In one embodiment, a *bacterium* which can be used as a biological weapon is stable or viable under a pressure above $5\times10^5$ Pa, $10\times10^5$ Pa, $15\times10^5$ Pa, $20\times10^5$ Pa, $30\times10^5$ Pa, $40\times10^5$ Pa, $50\times10^5$ Pa, $75\times10^5$ Pa, or $100\times10^5$ Pa. In another embodiment, a *bacterium* which can be used as a biological weapon is stable or viable under a pressure below $0.5\times10^5$ Pa, $0.2\times10^5$ Pa, $0.1\times10^5$ Pa, $0.05\times10^5$ Pa, $0.02\times10^5$ Pa, $0.01\times10^5$ Pa, $0.005\times10^5$ Pa, $0.002\times10^5$ Pa, or $0.001\times10^5$ Pa. Inn one embodiment, a *bacterium* which can be used as a biological weapon is stable or viable at a pH above 8.0, 8.5, 9.0, 9.5, 10.0, 105, 11.0, 11.5, 12.0, 112, 3.0, 13.5, or 14.0. In another embodiment, a *bacterium* which can be used as a biological weapon is stable or viable at a β below 6.0, 5.5, 5.0, 4.5, 4.0, 3.5, 3.0, 2.5, 2.0, 1.5, 1.0, 0.5, or 0.0. In one embodiment, a *bacterium* which can be used as a biological weapon is stable or viable under a relative humidity of 10%, 20%, 30%, 40%, 50%, 60%, 70%, 75%, 80%, 85%, 90%, 95%, or 99%. In another embodiment, a *bacterium* which can be used as a biological weapon is stable or viable under UV radiation, X-ray radiation, α radiation, β radiation, or γ radiation. In another embodiment, the *bacterium* is capable of infecting a subject after being treated with a combination of any of the aforementioned conditions.

In one embodiment, a *bacterium* which can be used as a biological weapon is able to form spores.

In another embodiment, a *bacterium* which can be used as a biological weapon can be dispersed in air or in liquid. In one embodiment, the *bacterium* is in a form of an aerosol (e.g., the *bacterium* is formulated as an aerosol). In another embodiment, the *bacterium* is in a form of powder (e.g., the *bacterium* is formulated as powder).

In one embodiment, a *bacterium* which can be used as a biological weapon includes a *bacterium* which is resistant to existing antibiotics, such as tetracycline antibiotics, including, but not limited to, tetracycline, doxycycline, minocycline, sancycline, methacycline, chlortetracycline, and deoxytetracycline, and a combination thereof, and other antibiotics, including but not limited to, aminoglycosides such as gentamicin and kanamycin, colistin, methicillin, vancomycin, penicillin, linezolid, fluoroquinolones such as ciprofloxacin, ceftazidime, and macrolides such as azithromycin. In a further embodiment, a *bacterium* which can be used as a biological weapon includes a *bacterium* which is resistant to gentamicin and/or colistin.

In one embodiment, a *bacterium* which can be used as a biological weapon includes, but is not limited to, a *bacterium* of the *Bacillus cereus* group (e.g., *Bacillus anthracis* and Multi Drug Resistant (MDR) *anthracis*), *Franciscella tularensis, Clostridium botulinum, Yersinia pestis, Burkholderia mallei, Burkholderia pseudomallei, Brucella* species, *Shigella* species, *Coxiella burnetii, Chlamydia psittaci, Clostridium perfringens, Rickettsia prowazekii,* Diarrheagenic *E. coli,* Pathogenic *Vibrios, Salmonella, Campylobacter jejuni, Yersinia enterocolitica,* and *Listeria monocytogenes.* In another embodiment, a *bacterium* which can be used as a biological weapon includes, but is not limited to, a *bacterium* of the *Bacillus cereus* group (e.g., *Bacillus anthracis* and Multi-Drug Resistant (MDR) *anthracis*), *Franciscella tularensis, Clostridium botulinum, Yersinia pestis, Burkholderia mallei, Brucella* species, *Shigella* species, *Coxiella burnetii, Chlamydia psittaci, Clostridium perfringens, Rickettsia prowazekii,* Diarrheagenic *E. coli,* Pathogenic *Vibrios, Salmonella, Campylobacter jejuni, Yersinia enterocolitica,* and *Listeria monocytogenes.*

In one embodiment, a *bacterium* which can be used as a biological weapon includes, but is not limited to, *Franciscella tularensis, Clostridium botulinum, Yersinia pestis, Burkholderia mallei, Burkholderia pseudomallei, Brucella* species *Shigella* species, *Coxiella burnetii, Chlamydia psittaci, Clostridium perfringens, Rickettsia prowazekii,* Diarrheagenic *E. coli,* Pathogenic *Vibrios, Salmonella, Campylobacter jejuni, Yersinia enterocolitica,* and *Listeria monocytogenes.* In another embodiment, a *bacterium* which can be used as a biological weapon includes, but is not limited to, *Franciscella tularensis, Clostridium botulinum, Yersinia pestis, Burkholderia mallei, Brucella* species, *Shigella* species, *Coxiella burnetii, Chlamydia psittaci, Clostridium perfringens, Rickettsia prowazekii,* Diarrheagenic *E. coli,* Pathogenic *Vibrios, Salmonella, Campylobacter jejuni, Yersinia enterocolitica,* and *Listeria monocytogenes.*

In a further embodiment, a *bacterium* which can be used as a biological weapon includes, but is not limited to, a *bacterium* of the *Bacillus cereus* group (e.g., *Bacillus anthracis* and Multi-Drug Resistant (MDR) *anthracis*), *Franciscella tularensis, Yersinia pestis, Burkholderia mallei, Burkholderia pseudomallei,* and *Rickettsia prowazekii.* In a further embodiment, a *bacterium* which can be used as a biological weapon includes, but is not limited to, a bacterium of the *Bacillus cereus* group (e.g., *Bacillus anthracis* and Multi-Drug Resistant (MDR) *anthracis*), *Franciscella tularensis, Yersinia pestis, Burkholderia mallei*, and *Rickettsia prowazekii*.

In a further embodiment, a *bacterium* which can be used as a biological weapon includes, but is not limited to, *Franciscella tularensis, Yersinia pestis, Burkholderia mallei, Burkholderia pseudomallei*, and *Rickettsia prowazekii*. In a further embodiment, a *bacterium* which can be used as a biological weapon includes, but is not limited to *Franciscella tularensis, Yersinia pestis, Burkholderia mallei*, and *Rickettsia prowazekii*.

In a further embodiment, a *bacterium* which can be used as a biological weapon is *Bacillus anthracis* or Multi-Drug Resistant (MDR) *anthracis*.

In yet a further embodiment, a *bacterium* which can be used as a biological weapon is *Burkholderia pseudomallei*.

The *Bacillus cereus* group of bacteria is composed of *Bacillus anthracis* (the etiologic agent of anthrax), *Bacillus cereus, Bacillus weihenstephanesis* (a food borne pathogen), *Bacillus thuringiensis* (an insect pathogen), and *Bacillus mycoides*.

In one embodiment, a *bacterium* which can be used as a biological weapon includes, but is not limited to, gram-positive pathogens, gram-negative pathogens, anaerobic pathogens, or atypical pathogens, or a combination thereof, including but not limited to, methicillin-susceptible *Staphylococcus aureus* (MSSA), methicillin-resistant *Staphylococcus aureus* (MRSA), susceptible *Staphylococcus aureus*, oxacillin-resistant *Staphylococcus aureus*, oxacillin-resistant coagulase-negative *Staphylococcus, Enterococcus faecalis, Enterococcus faecium*, vancomycin-susceptible *Enterococcus faecium*, vancomycin-resistant *Enterococcus faecium*, vancomycin-susceptible *Enterococcus faecalis*, vancomycin-resistant *Enterococcus faecalis, Streptococcus pneumoniae*, penicillin-susceptible *Streptococcus pneumonia*, penicillin-resistant *Streptococcus pneumoniae* (PRSP), *Streptococcus pyogenes, Streptococcus agalactiae, Haemophilus influenzae, Moraxella catarrhalis, Neisseria gonorrhoeae, Escherichia coli*, spp., *Salmonella* spp., *Klebsiella pneumoniae, Enterobacter aerogenes, Enterobacter cloacae, Serratia marcescens, Acinetobacter baumannii, Stenotrophomonas maltophilia, Bacteroides fragilis, Clostridium perfringens, Chlamydia pneumoniae, Legionella pneumophila, Proteus mirabilis, Pseudomonas aeruginosa*, and *Burkholderia cepacia*.

In one embodiment, the invention pertains, at least in part, to a method of treating a bacterial infection in a subject, comprising administering to the subject an effective amount of one or more compounds selected from Compounds 14-17 disclosed herein, stereoisomers, tautomers, and salts thereof, wherein the bacterial infection is caused by a *bacterium* selected from the group consisting of a *bacterium* of the *Bacillus cereus* group (e.g., *Bacillus anthracis* and Multi-Drug Resistant (MDR) *anthracis*), *Franciscella tularensis, Clostridium botulinum, Yersinia pestis, Burkholderia mallei, Burkholderia pseudomallei, Brucella* species, *Shigella* species, *Coxiella burnetii, Chlamydia psittaci, Clostridium perfringens, Rickettsia prowazekii*, Diarrheagenic *E. coli*, Pathogenic *Vibrios, Salmonella, Campylobacter jejuni, Yersinia enterocolitica*, and *Listeria monocytogenes*. In another embodiment, a *bacterium* which can be used as a biological weapon is selected from the group consisting of a *bacterium* of the *Bacillus cereus* group (e.g., *Bacillus anthracis* and Multi-Drug Resistant (MDR) *anthracis*), *Franciscella tularensis, Clostridium botulinum, Yersinia pestis, Burkholderia mallei, Brucella* species, *Shigella* species, *Coxiella burnetii, Chlamydia psittaci, Clostridium perfringens, Rickettsia prowazekii*, Diarrheagenic *E. coli*, Pathogenic *Vibrios, Salmonella, Campylobacter jejuni, Yersinia enterocolitica*, and *Listeria monocytogenes*. In yet another embodiment, a *bacterium* which can be used as a biological weapon is selected from the group consisting of *Franciscella tularensis, Clostridium botulinum, Yersinia pestis, Burkholderia mallei, Burkholderia pseudomallei, Brucella* species, *Shigella* species, *Coxiella burnetii, Chlamydia psittaci, Clostridium perfringens, Rickettsia prowazekii*, Diarrheagenic *E. coli*, Pathogenic *Vibrios, Salmonella, Campylobacter jejuni, Yersinia enterocolitica*, and *Listeria monocytogenes*. In a further embodiment, a *bacterium* which can be used as a biological weapon is selected from the group consisting of *Franciscella tularensis, Clostridium botulinum, Yersinia pestis, Burkholderia mallei, Brucella* species, *Shigella* species, *Coxiella burnetii, Chlamydia psittaci, Clostridium perfringens, Rickettsia prowazekii*, Diarrheagenic *E. coli*, Pathogenic *Vibrios, Salmonella, Campylobacter jejuni, Yersinia enterocolitica*, and *Listeria monocytogenes*. In a further embodiment, a *bacterium* which can be used as a biological weapon is selected from the group consisting of a *bacterium* of the *Bacillus cereus* group (e.g., *Bacillus anthracis* and Multi-Drug Resistant (MDR) *anthracis*), *Franciscella tularensis, Yersinia pestis, Burkholderia mallei, Burkholderia pseudomallei*, and *Rickettsia prowazekii*. In another embodiment, a *bacterium* which can be used as a biological weapon is selected from the group consisting of a *bacterium* of the *Bacillus cereus* group (e.g., *Bacillus anthracis* and Multi-Drug Resistant (MDR) *anthracis*), *Franciscella tularensis, Yersinia pestis, Burkholderia mallei*, and *Rickettsia prowazekii*. In a further embodiment, a *bacterium* which can be used as a biological weapon is selected from the group consisting of *Franciscella tularensis, Yersinia pestis, Burkholderia mallei, Burkholderia pseudomallei*, and *Rickettsia prowazekii*. In a further embodiment, a *bacterium* which can be used as a biological weapon is selected from the group consisting of *Franciscella tularensis, Yersinia pestis, Burkholderia mallei*, and *Rickettsia prowazekii*. In yet another embodiment, a *bacterium* which can be used as a biological weapon is *Bacillus anthracis* or Multi-Drug Resistant (MDR) *anthracis*.

In one embodiment, the invention pertains, at least in part, to a method of preventing a bacterial infection in a subject, comprising administering to the subject an effective amount of one or more compounds selected from Compounds 14-17 disclosed herein, including stereoisomers, tautomers, and salts thereof, wherein the bacterial infection is caused a *bacterium* selected from the group consisting of a *bacterium* of the *Bacillus cereus* group (e.g., *Bacillus anthracis* and Multi-Drug Resistant (MDR) *anthracis*), *Franciscella tularensis, Clostridium botulinum, Yersinia pestis, Burkholderia mallei, Burkholderia pseudomallei, Brucella* species, *Shigella* species, *Coxiella burnetii, Chlamydia psittaci, Clostridium perfringens, Rickettsia prowazekii*, Diarrheagenic *E. coli*, Pathogenic *Vibrios, Campylobacter jejuni, Yersinia enterocolitica*, and *Listeria monocytogenes*. In another embodiment, a *bacterium* which can be used as a biological weapon is selected from the group consisting of a *bacterium* of the *Bacillus cereus* group (e.g. *Bacillus anthracis* and Multi-Drug Resistant (MDR) *anthracis*), *Franciscella tularensis, Clostridium botulinum, Yersinia pestis, Burkholderia mallei, Brucella* species, *Shigella* species, *Coxiella burnetii, Chlamydia psittaci, Clostridium perfringens, Rickettsia prowazekii*, Diarrheagenic *E. coli*, Pathogenic *Vibrios, Salmonella, Campylobacter jejuni, Yersinia enterocolitica*, and *Listeria monocytogenes*. In yet another embodiment, a *bacterium* which can be used as a biological weapon is selected from the group consisting of *Franciscella tularensis, Clostridium botulinum, Yersinia pestis, Burkholderia mallei, Burkholderia pseudomallei, Brucella* species, *Shigella* species, *Coxiella burnetii, Chlamydia psittaci, Clostridium perfringens, Rickettsia prowazekii,* Diarrheagenic *E. coli,* Pathogenic *Vibrios, Salmonella, Campylobacter jejuni, Yersinia enterocolitica,* and *Listeria monocytogenes*. In a further embodiment, a *bacterium* which can be used as a biological weapon is selected from the group consisting of *Franciscella tularensis, Clostridium botulinum, Yersinia pestis, Burkholderia mallei, Brucella* species, *Shigella* species, *Coxiella burnetii, Chlamydia psittaci, Clostridium perfringens, Rickettsia prowazekii,* Diarrheagenic *E. coli,* Pathogenic *Vibrios, Salmonella, Campylobacter jejuni, Yersinia enterocolitica,* and *Listeria monocytogenes*. In yet a further embodiment, a *bacterium* which can be used as a biological weapon is selected from the group consisting of a *bacterium* of the *Bacillus cereus* group (e.g., *Bacillus anthracis* and Multi-Drug Resistant (MDR) *anthracis*), *Franciscella tularensis, Yersinia pestis, Burkholderia mallei, Burkholderia pseudomallei,* and *Rickettsia prowazekii*. In another embodiment, a *bacterium* which can be used as a biological weapon is selected from the group consisting of a *bacterium* of the *Bacillus cereus* group (e.g., *Bacillus anthracis* and Multi-Drug Resistant (MDR) *anthracis*), *Franciscella tularensis, Yersinia pestis, Burkholderia mallei,* and *Rickettsia prowazekii*. In a further embodiment, a *bacterium* which can be used as a biological weapon is selected from the group consisting of *Franciscella tularensis, Yersinia pestis, Burkholderia mallei, Burkholderia pseudomallei,* and *Rickettsia prowazekii*. In a further embodiment, a *bacterium* which can be used as a biological weapon is selected from the group consisting of *Franciscella tularensis, Yersinia pestis, Burkholderia mallei,* and *Rickettsia prowazekii*. In a further embodiment, a *bacterium* which can be used as a biological weapon is *Bacillus anthracis* or Multi-Drug Resistant (MDR) *anthracis*.

In one embodiment, treating a microbial (e.g., bacterial) infection in a subject comprises administering a compound of the present invention after the subject's exposure to the microorganism, e.g., a *bacterium*, but before the subject develops any symptom of the microbial (e.g., bacterial) infection. In one embodiment, a compound of the present invention is administered about 10 min, 20 min, 30 min, 40 min, 50 min, 1 hr, 2 his, 3 his, 6 his, 12 hrs, 18 his, 24 hrs, 36 his, 48 his, 72 his, 96 hrs, 1 week, or 2 weeks after the subject's exposure but before the subject develops any symptom. In another embodiment, treating a microbial bacterial) infection in a subject comprises administering a compound of the present invention after the subject develops a symptom after the subject's exposure to the microorganism. In one embodiment, a compound of the present invention is administered 10 min, 20 min, 30 min, 40 min, 50 min, 1 hr, 2 his, 3 his, 6 hrs, 12 hrs, 18 hrs, 24 hrs, 36 his, 48 hrs, 72 hrs, 96 hrs, 1 week, or 2 weeks after the subject develops a symptom.

In another embodiment, treating a microbial (e.g., bacterial) infection in a subject comprises administering a compound of the present invention after the subject's suspected exposure to the microorganism, e.g., a *bacterium*, but before the subject develops any symptom of the microbial infection. In one embodiment, the compound of the present invention is administered about 10 min, 20 min, 30 min, 40 min, 50 min, 1 hr, 2 hrs, 3 hrs, 6 hrs, 12 his, 18 his, 24 his, 36 hrs, 48 his, 72 hrs, 96 hrs, 1 week, or 2 weeks after the subject's suspected exposure but before the subject develops any symptom.

"Suspected exposure" means that there is certain possibility (e.g., 5%, 10%, 20%, 30%, 40%, 50%, 60%, 70%, 75%, 80%, 85%, 90%, 95%, and 99%), although it is not known, that a subject has been exposed to a microorganism, e.g., a *bacterium*, and thus is at the risk of a microbial (e.g., bacterial) infection. For example, "suspected exposure" means that there is greater than 50% possibility that a subject has been exposed to a microorganism, e.g., a *bacterium*.

"Symptom" of a microbial (e.g., bacterial) infection can be any indication that the subject exposed or suspected of being exposed to the *bacterium* is not normal, well, or comfortable, regardless of the subject's subjective perception or teeing, "Symptom" includes, but is not limited to, headache, stomachache, abdominal cramps, abdominal pain, muscle pain, fever, diarrhea, vomiting, coughing, weakness, tiredness, soreness, rash or bumps on skin, wounds in any parts of the body (skin, head, eye, ear, nose, mouth, torso, limbs, arm, hand, leg, foot, etc.), and an abnormality in any tissue or organ (skin, bone, blood, lymph, intestine, stomach, pancreas, brain, heart, lung, liver, spleen, kidney, bladder, ovary, etc.).

In one embodiment, preventing a microbial (e.g., bacterial) infection in a subject comprises administering a compound of the present invention before the subject's exposure to the microorganism, e.g., a *bacterium*. In one embodiment, the compound of the present invention is administered about 10 min, 20 min, 30 min, 40 min, 50 min, 1 hr, 2 his, 3 hrs, 6 hrs, 12 hrs, 18 hrs, 24 hrs, 36 hrs, 48 hrs, 72 hrs, 96 hrs, 1 week, or 2 weeks before the subject's exposure. In another embodiment, preventing a microbial (e.g., bacterial) infection in a subject comprises administering a compound of the present invention before or after an event which raises the risk of the subject being exposed to the microorganism. The event includes, but is not limited to, an attack (e.g., a terrorist attack) with a biological weapon and the subject's entry into a risky territory such as a battlefield. In one embodiment, a compound of the present invention is administered to the subject 10 min, 20 min, 30 min, 40 min, 50 min, 1 hr, 2 hrs, 3 hrs, 6 hrs, 12 his, 18 hrs, 24 hrs, 36 hrs, 48 hrs, 72 hrs, 96 hrs, 1 week, or 2 weeks before the event. In another embodiment, a compound of the present invention is administered to the subject 10 min, 20 min, 30 min, 40 min, 50 min, 1 hr, 2 his, 3 his, 6 hrs, 12 hrs, 18 hrs, 24 hrs, 36 hrs, 48 hrs, 72 hrs, 96 hrs, 1 week, or 2 weeks after the event.

In another embodiment, the method of the present invention may further comprise, before administering a compound of the present invention, identifying a subject at risk of being exposed to a microorganism (e.g., a *bacterium*) which can be used as a biological weapon. The subject at risk of being exposed to a microorganism (e.g., a *bacterium*) which can be used as a biological weapon includes, but is not limited to, a subject travelling to, entering, or being in a conflict region (e.g., a battlefield and combat zone), such as military personnel, intelligence personnel, and animals used in the military, a subject engaged or about to be engaged in a security operation, such as governmental authorities (e.g., police, governmental investigators, and secret service members) and other personnel (e.g., doctors, nurses, and rescue workers), and animals used in such an operation, and a subject in an geographical area that is likely to be a target of a terrorist attack (e.g., a metropolitan area, a city, an area where there is a large population (e.g., above 100,000, above 200,000, above 500,000, above 1 million, above 2 million, above 5 million, and above 10 million), and a location or area to which damage is likely to cause a threat to national security or public health (e.g., a nuclear power plant, a chemical plant, an airport, and a hospital)).

"Expose", "exposure", or "exposed" means that a subject comes in contact in any way with a *bacterium* or any component thereof (e.g., bacterial cell wall, bacterial cell membrane, a bacterial nucleic acid, a bacterial polynucleotide, a bacterial protein, a bacterial polypeptide, a bacterial spore, and a bacterial toxin). For example, a subject may be exposed to a *bacterium* or any component thereof by ingesting, inhaling, or touching anything which contains the *bacterium* or any component thereof *Bacterium* as well as components of a *bacterium* (e.g., bacterial cell wall, bacterial cell membrane, a bacterial nucleic acid, a bacterial polynucleotide, a bacterial protein, a bacterial polypeptide, a bacterial spore, and a bacterial toxin) can cause an infection or symptoms of an infection in a subject. An example of a bacterial component that can cause an infection is a bacterial spore.

In one embodiment, the invention pertains to a method of treating a bacterial infection in a subject, wherein the subject is exposed or suspected of being exposed to a *bacterium* or a component thereof, comprising administering to the subject an effective amount of a compound disclosed herein. In another embodiment, the invention pertains to a method of preventing a bacterial infection in a subject, wherein the subject is at a risk of being exposed to a *bacterium* or a component thereof, comprising administering to the subject an effective amount of a compound disclosed herein. In one embodiment, the *bacterium* or a component thereof is formulated as an aerosol or power. In another embodiment, the bacterial component is a bacterial spore.

In some embodiments, the effective amount of the compound used for the method of this invention ranges from 0.1 mg to 1500 mg, e.g., about 0.25 mg, about 0.5 mg, about 1 mg, about mg, about 2.5 mg, about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 tug, about 825 tug, about 850 mg, about 875 mg, about 900 mg, about 925 tug, about 950 mg, about 975 mg, about 1000 mg, about 1025 mg, about 1050, mg, about 1075 mg, about 11.00 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1.475 mg, or about 1500 mg.

In some embodiments, the compounds described herein are administered optically, ophthalmically, nasally, orally, parenterally, topically, or intravenously to a subject in need thereof.

In some embodiments, the present invention relates to a method of synthesizing a compound described herein.

In some embodiments, the present invention relates to a medical device containing a compound described herein. In some embodiments, the device is a stent.

The term "treating" or "treatment" refers to the amelioration or diminishment of one or more symptoms of the disorder, e.g., a microbial infection such as a bacterial infection, to be treated.

The term "prophylaxis", "prevent", or "prevention" means to prevent or reduce the risk of microbial infection such as a bacterial infection.

A *bacterium* is "easily produced or disseminated" if the *bacterium* can be produced or disseminated by routine methods, processes, or techniques and with common materials, reagents, equipment, etc. available in the art, or by methods, processes, or techniques and with materials, reagents, equipment, etc. which are accessible to and can be operated or used by a lay person having little or no training in the art.

The term "moderate morbidity" refers to morbidity of no less than 10%, no less than 15%, no less than 20%, no less than 25%, no less than 30%, no less than 35%, no less than 40%, or no less than 45%. The term "high morbidity" refers to morbidity of no less than 50%, no less than 55%, no less than 60%, no less than 65%, no less than 70%, no less than 75%, no less than 80%, no less than 85%, no less than 90%, or no less than 95%.

The term "moderate mortality" refers to mortality of no less than 10%, no less than 15%, no less than 20%, no less than 25%, no less than 30%, no less than 35%, no less than 40%, or no less than 45%. The term "high mortality" refers to mortality of no less than 50%, no less than 55%, no less than 60%, no less than 65%, no less than 70%, no less than 75%, no less than 80%, no less than 85%, no less than 90%, or no less than 95%.

The term "resistance" or "resistant" rears to the antibiotic/ organism standards as defined by the Clinical and Laboratories Standards Institute (CLSI) andlor the Food and Drug Administration (FDA).

As used herewith, the term "multi-drug resistance," "multi-drug resistant" or "MDR" refers to acquired non-susceptibility to at least two antimicrobial agents, e.g., resistance to one agent in three or more antimicrobial categories. The term "extremely-drug resistance" or "extensive drug resistance" or "XDR," as used herewith, refers to acquired non-susceptibility to at least one agent in all but two or fewer antimicrobial categories (i.e., bacterial isolates remain susceptible to only one or two categories). Accordingly, an XDR bacterial isolate is always a MDR bacterial isolate, but a MDR bacterial isolate is not necessarily an XDR bacterial isolate. For example, an XDR microorganism is a *Pseudomonas aeruginosa* isolate that is susceptible to only one or two antimicrobial categories such as a *Pseudomonas aeruginosa* isolate that is only susceptible to polymyxins (e.g., colistin) or only susceptible to a pyrrolocystine compound described herein (e.g., Compound 14) or those described in US 2012-0220566 or WO 2012/173689. See, e.g., Magiorakos et al., *Clin Microbial Infect.* 2012; 18: 268-281, the content of which is hereby incorporated by reference in its entirety.

The term "subject" includes animals which either have or are susceptible or are suspected to have acquired a microbial infection (e.g., a bacterial infection). Examples of subjects include animals such as farm animals (e.g., cows, pigs, horses, goats, rabbits, sheep, chickens, etc.), lab animals (mice, rats, monkeys, chimpanzees, etc.), pets (e.g., dogs, cats, ferrets, hamsters, etc.), birds (e.g., chickens, turkeys, ducks, geese, crows, ravens, sparrows, etc.), primates (e.g., monkeys, gorillas, chimpanzees, bonobos, and humans), and other animals (e.g., squirrels, raccoons, mice, rats, etc.). In another embodiment, the subject is a mouse or rat. In yet another embodiment, the subject is a cow, a pig, or a chicken. In another embodiment, the subject is a human.

The compounds of the present invention may be administered by any route which allows the compounds to perform their intended function, e.g., treat or prevent a bacterial infection. Examples of routes include, but are not limited to, orally, intravenously, and topically. In one embodiment, a compound of the present invention is administered orally. In another embodiment, a compound of the present invention is administered intravenously.

The term "effective amount" includes the amount of a compound of the present invention needed to treat or prevent a bacterial infection. For example, an effective amount describes an amount that produces an efficacious level sufficient to achieve the desired therapeutic effect through the killing of bacteria and/or inhibition of bacterial growth. In one embodiment, the effective amount is sufficient to eradicate the *bacterium* or bacteria causing the infection.

The term "about" refers to a range of values which can be 15%, 10%, 8%, 5%, 3%, 2%, 1%, or 0.5% more or less than the specified value. For example, "about 10%" can be from 8 to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

The structures of the compounds of the present invention may include double bonds or asymmetric carbon atoms. Such compounds can occur as racemates, racemic mixtures, single enantiomers, individual diastereomers, diastereomeric mixtures, and cis- or trans- or E- or Z-double bond isomeric forms. Such isomers can be obtained in substantially pure form by classical separation techniques and/or by stereochemically controlled synthesis. Furthermore, the structures of the compounds and moieties discussed in the present invention also include all to homers thereof.

Some compounds of the present invention can exist in one or more tautomeric forms. "Tautomers" refer to compounds whose structures differ markedly in the arrangement of atoms, but which exist in easy and rapid equilibrium is to be understood that compounds of present invention may be depicted as different tautomers. It should also be understood that when compounds have tautomeric forms, all tautomeric forms are intended to be within the scope of the invention, and the naming of the compounds does not exclude any tautomeric form.

The compounds, pharmaceutically acceptable salts, esters and prodrugs of the present invention can exist in one or more tautomeric forms, including the enol and imine form, and the keto and enamine form and geometric isomers and mixtures thereof. All such tautomeric forms of the compounds described herein are included within the scope of the present invention. Tautomers exist as mixtures of a tautomeric set in solution. In solid form, usually one tautomer predominates. Even though one tautomer may be described, the present invention includes all tautomers of the present compounds.

A "tautomer" is one of two or more structural isomers that exist in equilibrium and are readily converted from one isomeric form to another. This isomerization results in the formal migration of a hydrogen atom accompanied by a shift of adjacent conjugated double bonds. In solutions where tautomerization is possible, a chemical equilibrium of the tautomers can be reached. The exact ratio of the tautomers depends on several factors, including temperature, solvent, and pH. The concept of interconvertable tautomers by tautomerizations is called tautomerism.

Of the various types of tautomerism that are possible, two are commonly observed. In keto-enol tautomerism, a simultaneous shift of electrons and a hydrogen atom occurs. Ring-chain tautomerism, exhibited by glucose and other sugars, arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); and 3. protonation at a different position of the anion; Acid: 1. protonation; 2. formation of a delocalized cation; and 3. deprotonation at a different position adjacent to the cation.

Common tautomeric pairs include: ketone-enol, amide-nitrite, lactam lactim, amide-imidic acid tautomerism in heterocyclic rings (e.g. in the nucleobases guanine, thymine, and cytosine), amine-enamine and enamine-enamine. An example below is included for illustrative purposes, and the present invention is not limited to this example:

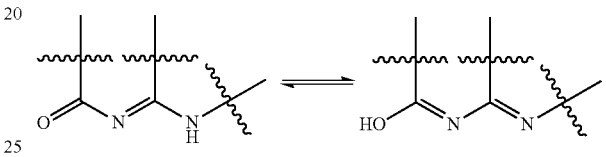

The compounds of the present invention may be basic or acidic, and are capable of forming a wide variety of salts with various acids or bases. The compounds of the present invention that are acidic in nature are capable of forming a wide variety of salts with various bases. The bases that may be used to prepare pharmaceutically acceptable salts of the compounds of the present invention that are acidic include those bases that form non-toxic base salts, such as salts containing alkali metal cations (e.g., $Na^+$ and $K^+$), alkaline earth metal cations (e.g., $Mg^{-+}$ and $Ca^{++}$), and amines.

The compounds of the present invention that are basic in nature are capable of forming a wide variety of salts with various inorganic and organic acids. The acids that may be used to prepare pharmaceutically acceptable acid addition salts of the compounds of the present invention that are basic in nature include those acids that form nontoxic acid addition salts, i.e., salts containing pharmaceutically acceptable anions, such as the hydrochloride (HCl hydrobromide (HBr salt), hydroiodide (HI salt), nitrate, sulfate, bisulfate, phosphate, acid phosphate, isonicotinate, acetate, lactate, salicylate, citrate, acid citrate, tartrate, bitartrate, pantothenate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate (i.e., tosylate), and palmoate (i.e., 1,1'-methylene-bis-(2 hydroxy-3-naphthoate)) salts. Although such salts must be pharmaceutically acceptable for administration to a subject, e.g., an animal, it is often desirable in practice to initially isolate the compounds of the present invention from the reaction mixture as pharmaceutically unacceptable salts and then simply convert the latter back to the free, base compounds by treatment with an alkaline reagent and subsequently convert the latter free base to pharmaceutically acceptable acid addition salts.

The acid addition salts of the compounds of the present invention are readily prepared by treating the compounds with a substantially equivalent amount of the chosen mineral or organic acid in an aqueous solvent medium or in a suitable organic solvent, such as methanol or ethanol. Upon careful evaporation of the solvent, the desired solid salts are readily obtained.

In cases where the compounds suitable for the methods of the invention contain nitrogen atoms, these compounds, where appropriate, can be converted to N-oxides by treatment with an oxidizing agent (e.g., meta-chloroperoxybenzoic acid (mCPBA) and/or hydrogen peroxides). Thus, compounds containing nitrogen atoms shown and claimed are considered to cover both the nitrogen containing compound and its N-oxide (N→O) derivative, as appropriate. In some embodiments, the present invention relates to N-oxides of the compounds or tautomers thereof, or pharmaceutically acceptable salts, esters, or prodrugs of said compounds or tautomers thereof, disclosed herein.

The invention also comprises isotopically-labeled compounds of the present invention and their use thereof, which are identical to those recited in formulae of the invention, but for the replacement of one or more atoms by an atom having an atomic mass or mass number different from the atomic mass or mass number most commonly found in nature. Examples of isotopes that can be incorporated into compounds of the present invention or tautomers thereof, or pharmaceutically acceptable salts, esters, or prodrugs of said compounds or tautomers include isotopes of hydrogen, carbon, nitrogen, fluorine, such as $^3$H, $^{11}$C, $^{14}$C and $^{18}$F.

The compounds of the present invention that contain the aforementioned isotopes and/or isotopes of other atoms are within the scope of the present invention. Isotopically-labeled compounds, for example, include those compounds into which radioactive isotopes such as $^3$H and $^{14}$C are incorporated and/or are useful in drug and/or substrate tissue distribution assays. Tritium, i.e., $^3$H, and carbon-14, i.e., $^{14}$C, isotopes are particularly preferred due to their ease of preparation and detectability. $^{11}$C and $^{18}$F isotopes are particularly useful in PET (positron emission tomography). PET is useful in brain imaging. Furthermore, substitution with heavier isotopes such as deuterium, i.e., $^2$H, can afford certain therapeutic advantages including greater metabolic stability, i.e., increased in vivo half-life or reduced dosage requirements and, hence, may be preferred in some circumstances. Isotopically labeled compounds of the invention or tautomers thereof, or pharmaceutically acceptable salts, esters, or prodrugs of said compounds or tautomers can generally be prepared as described in the procedures, Schemes and/or in the Examples disclosed herein, by substituting a non-isotopically labeled reagent with a readily available isotopically labeled reagent. In one embodiment, the compounds or tautomers thereof, or pharmaceutically acceptable salts, esters, or prodrugs of said compounds or tautomers of the invention are not isotopically labeled.

It is to be understood that wherever values and ranges are provided herein, e.g., in ages of subject populations, dosages, and time durations, etc., all values and ranges encompassed by these values and ranges, are meant to be encompassed within the scope of the present invention. Moreover, all values in these values and ranges may also be the upper or lower limits of a range.

The compounds of the present invention can be synthesized by any techniques known in the art, such as those described in US 2012-0220566 and WO 2012/173689, the contents of which are incorporated herein by reference in their entirety. The compounds thus obtained can be further purified, for example, by flash column chromatography, high performance liquid chromatography, crystallization, or any known purification method.

In one embodiment, the compounds of the present invention can be synthesized according to the synthetic Schemes 1-5 below:

Scheme 1

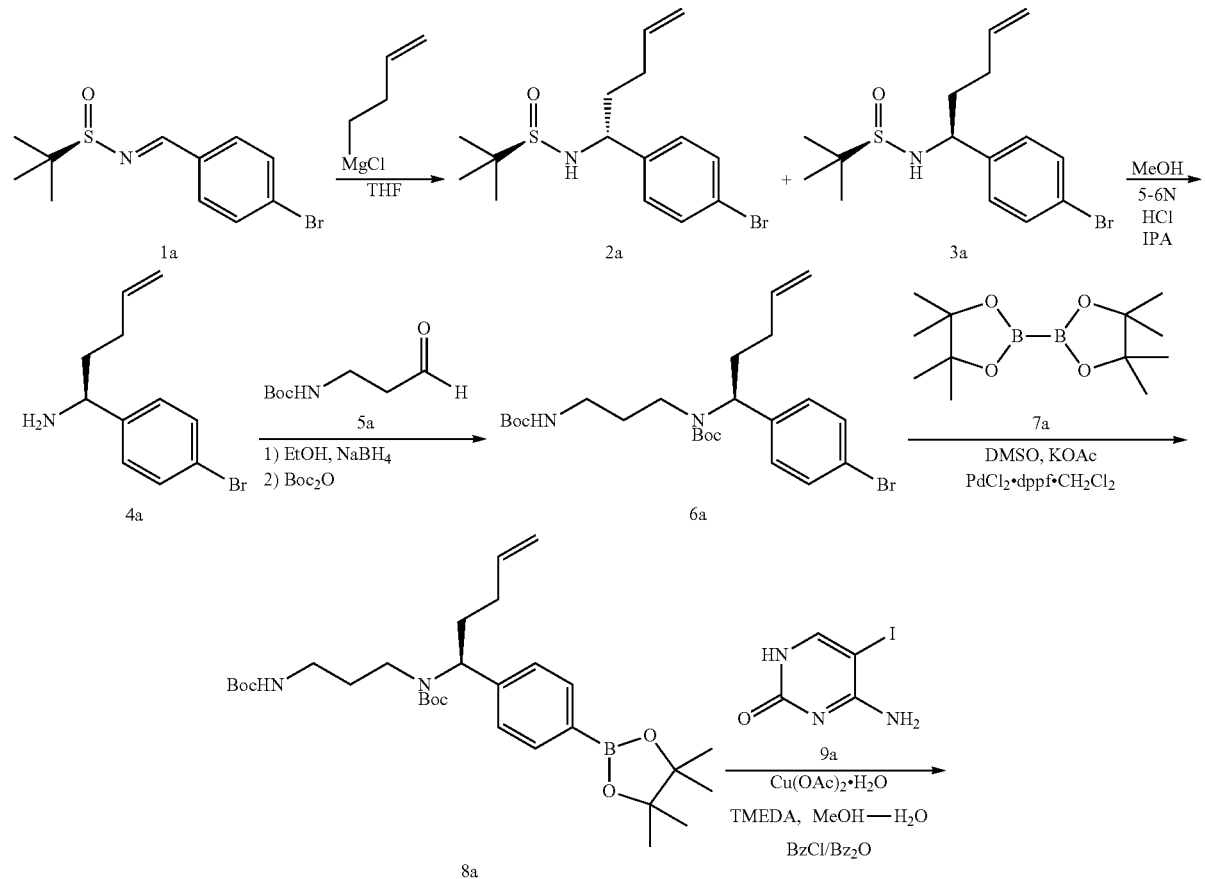

-continued

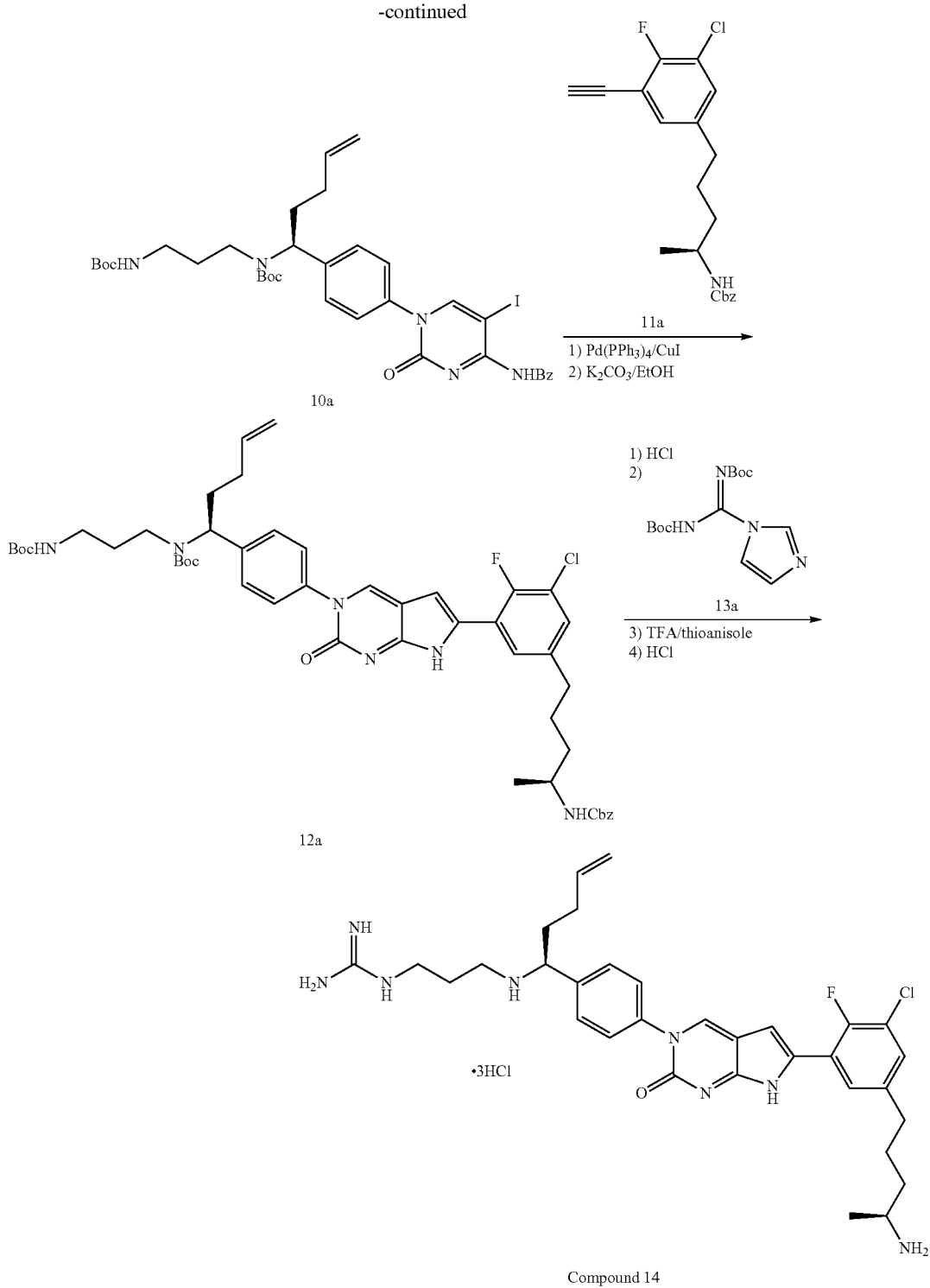

Compound 14

As shown in Scheme 1 above, pyridine para-toluenesulfonate and magnesium sulfate are added to a solution of (R)-(+)-2-methyl-2-propanesulfinamide and 4-bromobenzaldehyde in solvent, e.g., dichloromethane and the resulting mixture is stirred overnight at ambient temperature. The mixture is then filtered, concentrated, and purified by flash chromatography, e.g., over silica gel (5% ethyl acetate in dichloromethane), to afford compound 1a. A solution of compound 1a in tetrahydrofuran (THF) is then treated with 3-butenyl magnesium bromide at, e.g., −75° C. The resulting mixture is then slowly warmed up to ambient temperature and stirred overnight. The reaction is then quenched with saturated ammonium chloride solution, extracted with an organic solvent, e.g., ethyl acetate and the combined organic layers are then dried (with, e.g., anhydrous sodium sulfate), concentrated, and purified to yield 2a and 3a. Compound 3a in methanol is then treated with an acid, e.g., 5-6 N HCl in isopropanol, to afford amine 4a as a hydrochloride salt.
Compound 4a is then converted to Compound 14 (ESI, m/z 607.1 [M+H]$^+$) as shown Scheme 1 above using a method similar to that described in WO 2012/173689.
Scheme 2
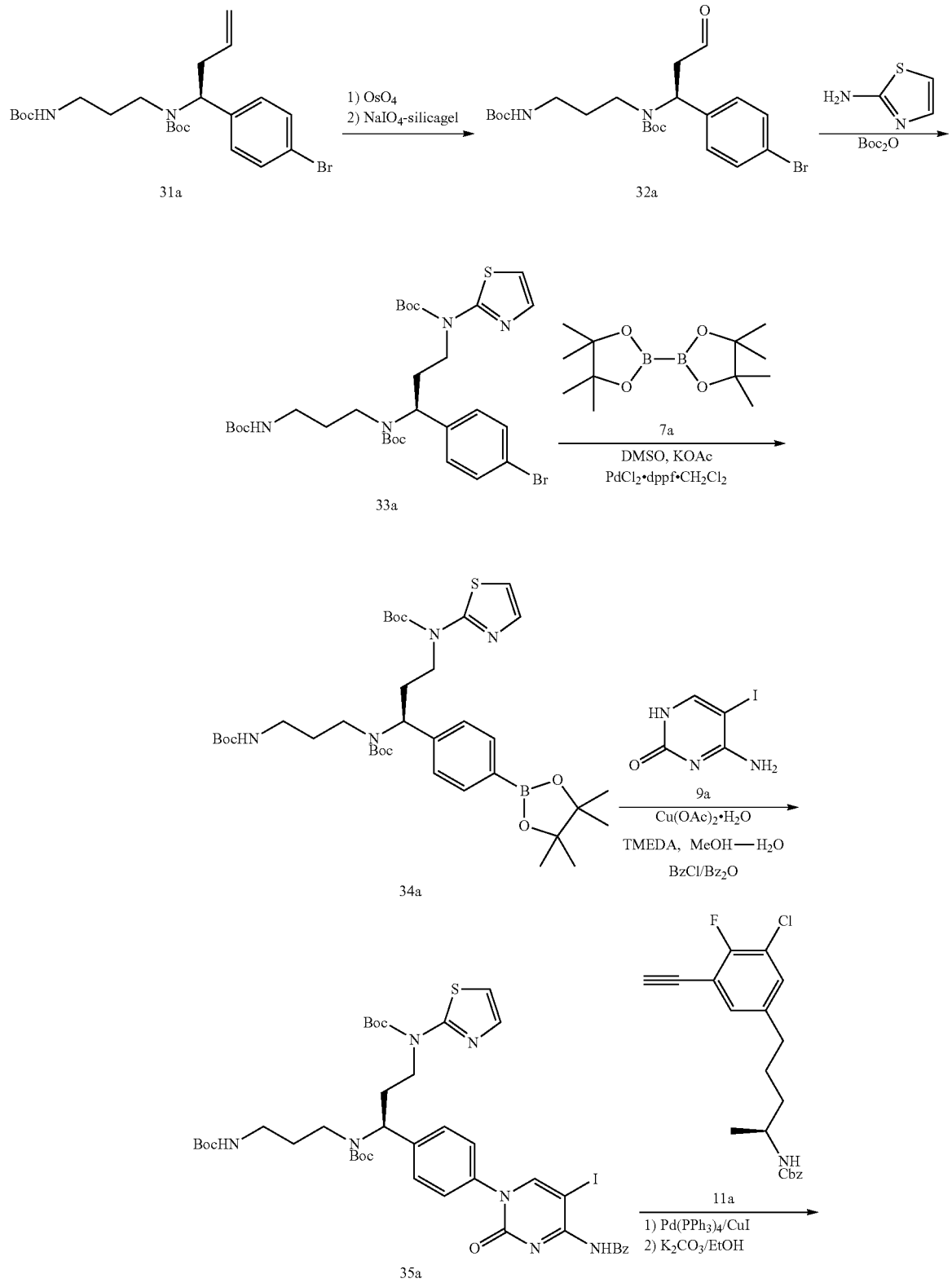

-continued

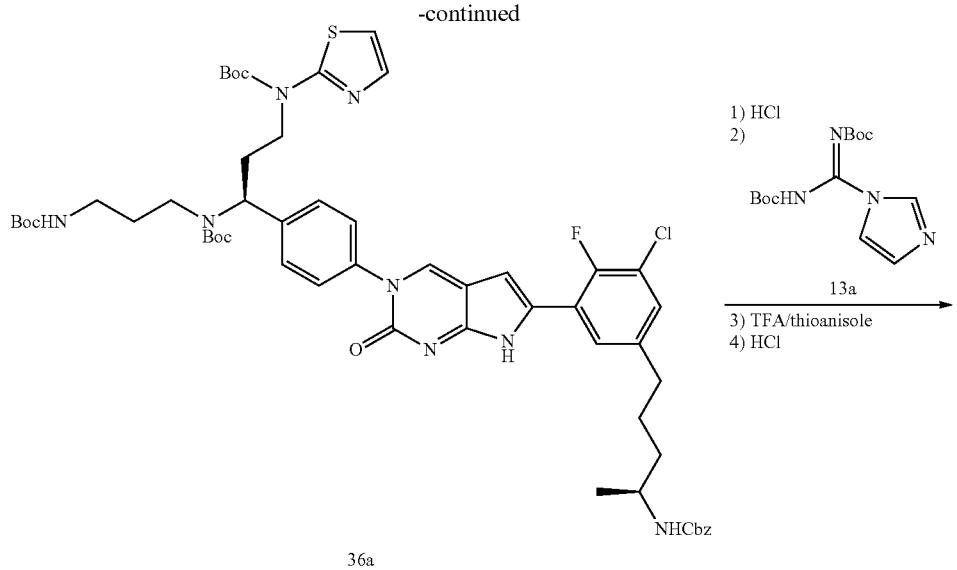

36a

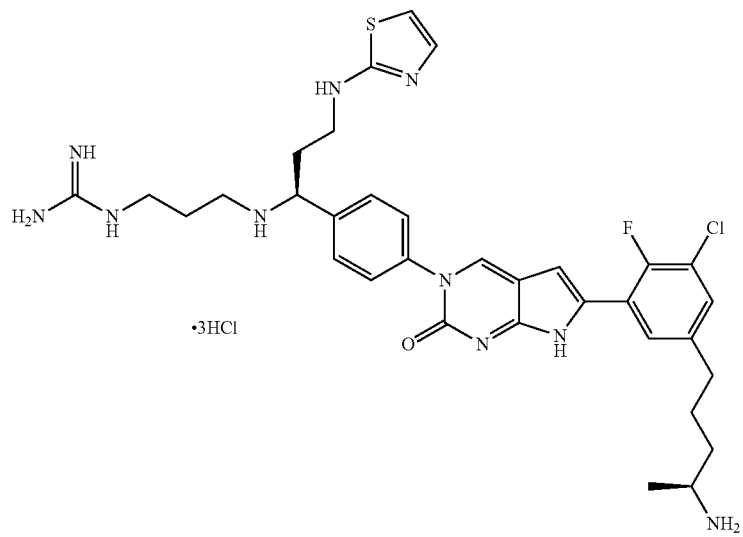

Compound 15

Compound 31a is synthesized using a method similar to that used to synthesize compound ba in Scheme 1. As shown in Scheme 2, Compound 31a is converted to aldehyde 32a by oxidation of the olefin, e.g., with osmium tetroxide ($OsO_4$) and sodium periodate-silica gel ($NaIO_4$—$SiO_2$).

Aldehyde 32a can then undergo reductive amination with 2-amino thiazole followed by protection of the resulting amine to provide 33a. This intermediate can then be converted to Compound 15 (ESI, m/z 340.1 $[M+H]^{+2}$) using a method similar to that d scribed in WO 2012/173689.

Scheme 3

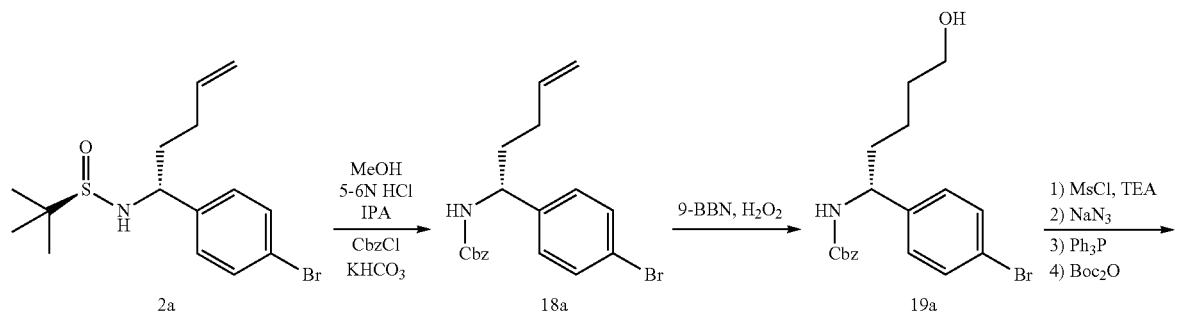

-continued
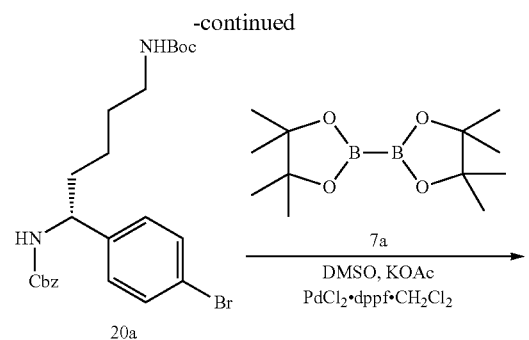
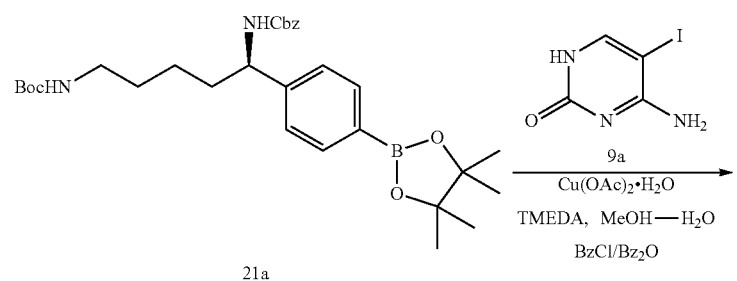
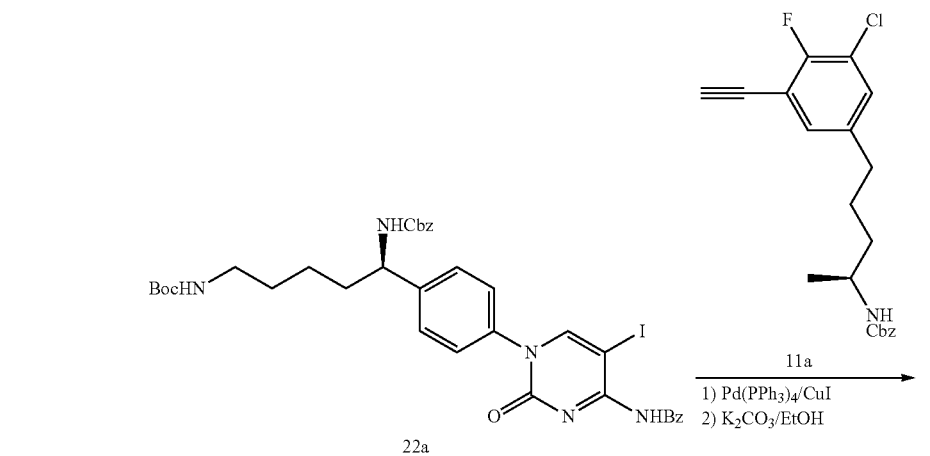
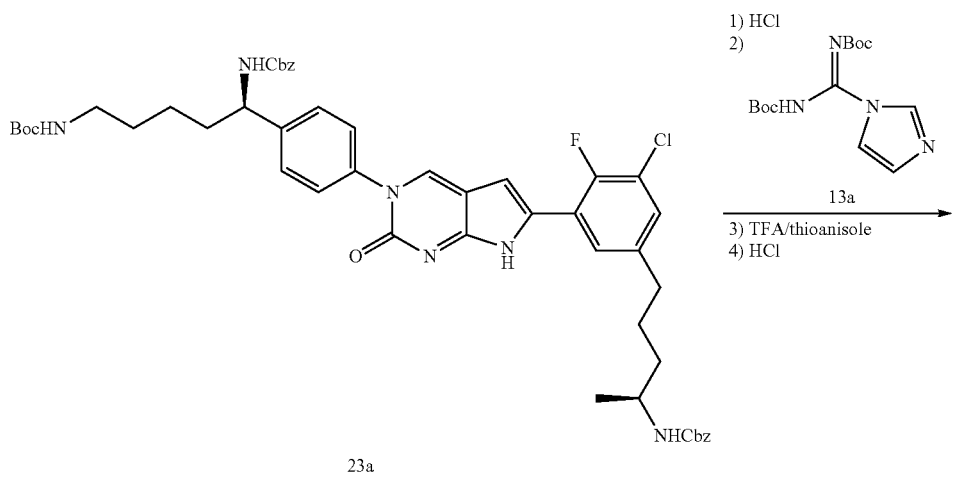

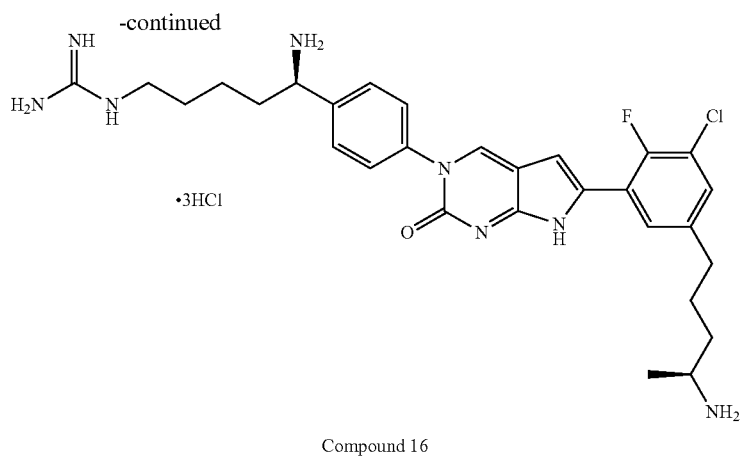

Compound 16

As shown in Scheme 3, compound 2a as a solution in a solvent, e.g., methanol (MeOH), is treated with acid, e.g., 5-6 N HCl in isopropanol, followed by benzyl chloroformate (Cbz-Cl) and potassium bicarbonate (KHCO$_3$) to provide protected amine 18a. To a solution of 18a in tetrahydrofuran (THF) is then added 9-Borabicyclo(3.3.1)nonane (9-BBN) and the resulting mixture is stirred overnight at ambient temperature. The solution is then quenched with hydrogen peroxide and upon workup affords 19a. Alcohol 19a is then converted to 20a using standard synthetic protocols as shown in Scheme 3. Conversion of compound 20a to Compound 16 (ESI, m/z 567.1 [M+H]$^+$) can be accomplished using a method similar to that described in WO 2012/173689.

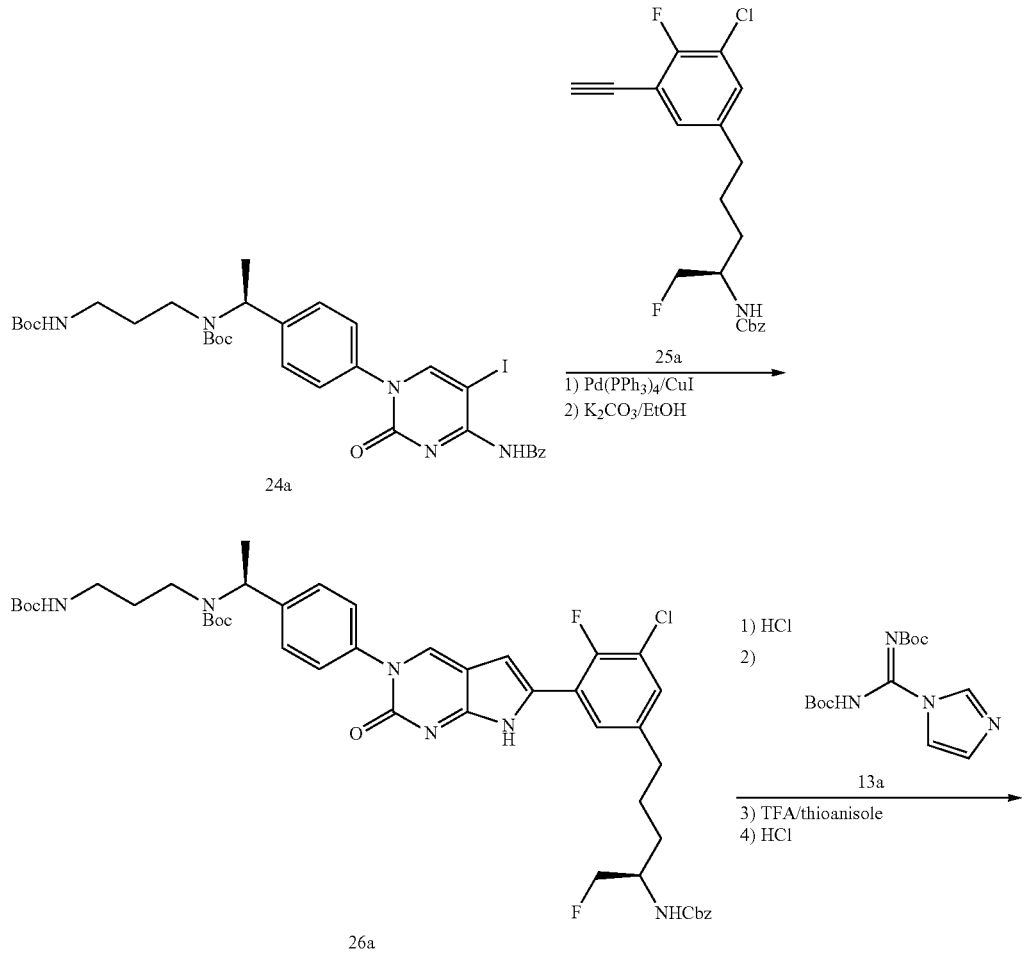

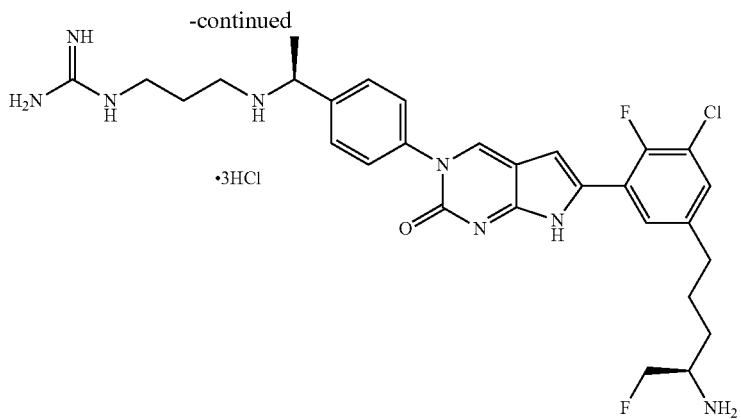

Compound 17

As shown in Scheme 4, Compound 17 (ESI, m/z 585.1 [M+H]$^+$) is synthesized from intermediate 24a (synthesis of which is described in WO 2012/173689) using a method similar to those that described in WO 2012/173689. Alkyne derivative 25a can be made using the procedure shown in Scheme 5 below.

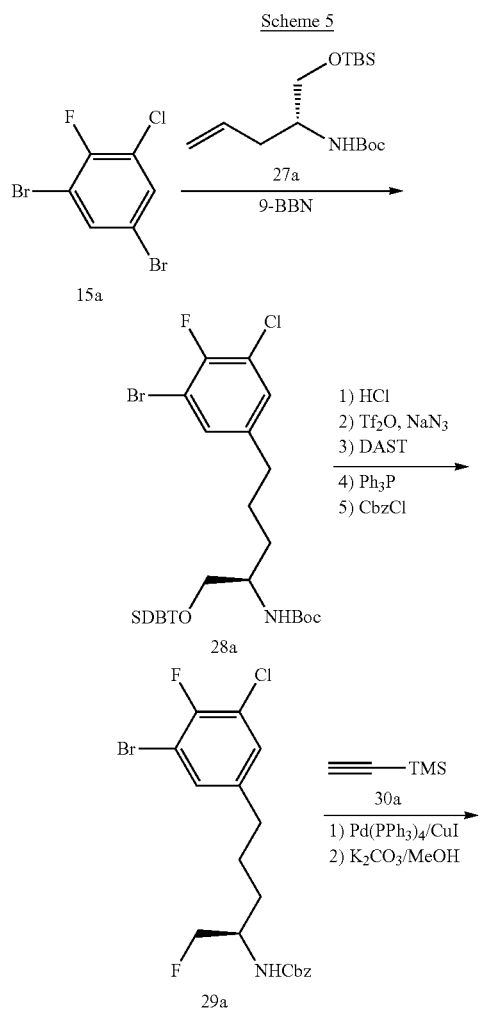

Scheme 5

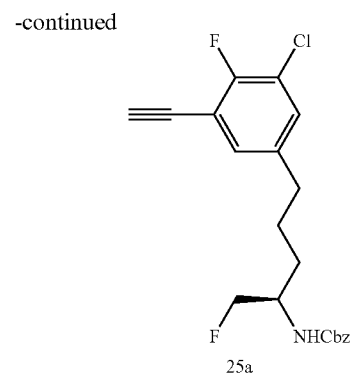

25a

9-Borabicyclo(3.3.1)nonane (9-139N) is added to a solution of 27a in solvent, e.g., toluene and THF, and the resulting mixture is stirred overnight at ambient temperature. The reaction mixture is then concentrated and 15a in toluene and 1N sodium hydroxide (NaOH) is added followed by palladium tetrakis (Pd(PPh$_3$)$_4$). The resulting mixture is then heated at an elevated temperature, e.g., 60° C., for 24 hours. After standard work up and purification procedures, 28a is obtained. Addition of acid, e.g., 6 N HCl to intermediate 28a to form the corresponding amino alcohol followed by subsequent treatment with trifluoromethyl sulfonic anhydride and sodium azide afforded the corresponding azide. The azide is then treated with diethylaminosulfur trifluoride (DAST) followed by triphenyl phosphine and benzyl chloroformate (Cbz-Cl) to afford 29a. The polyhalogenated derivative 29a is then coupled to 30a using standard coupling conditions to provide 25a.

The reagents used in the synthetic routes described in the above patents may include, for example, solvents, reagents, catalysts, and protecting group and deprotecting group reagents. The synthetic routes may also include additional steps, either before or after the steps described specifically therein, to add or remove suitable protecting groups in order to ultimately allow synthesis of the desired pyrrolocytosine compounds. In addition, various synthetic steps may be performed in an alternate sequence or order to provide the desired compounds. For example, compounds may be further modified via conventional chemical transformations to produce the compounds of the present invention. Synthetic chemistry transformations and protecting group methodologies (protection and deprotection) are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The synthetic routes described in the above patents are used only for illustrative purposes. One skilled in the art, in view of the schemes and the examples provided herein, would appreciate that all of the compounds of the present invention can be made by similar methods that are well known in the art.

The efficacy of the compounds of the present invention in treating, preventing, reducing the risk of, or delaying the onset of a bacterial infection may be assessed by using common methods known in the art. In one embodiment, the efficacy may be determined by a Minimum Inhibition Concentration (MIC) assay. For example, the compound of the present invention is serially diluted and then added to the growth medium (e.g., cation-adjusted Mueller Hinton broth (CAMHB)) of the bacterial culture. The lowest concentration of the compound of the present invention that inhibits 50% or 90% bacterial growth (i.e., $MIC_{50}$ or $MIC_{90}$) is determined and, if necessary, is compared with the $MIC_{50}$ or $MIC_{90}$ of other antibiotics. In another embodiment, the efficacy may be determined through in vivo assays known in the art (e.g., animal experiment). For example, a compound of the present invention is administered to experimental animals (e.g., mice and rats) at decreasing amounts. The lowest amount of the compound of the present invention that treats the experimental animal (e.g., ameliorates symptoms of a bacterial infection, prolongs the survival time of the animal, and allows animal to survive the bacterial infection) or prevents the experimental animals from being infected by the *bacterium* or developing any symptoms of the infection is determined and, if necessary, is compared with the lowest amount of other antibiotics which achieves the same results.

The invention also pertains to pharmaceutical compositions comprising a therapeutically effective amount of a compound described herein (e.g., Compound 14) or a salt thereof and, optionally, a pharmaceutically acceptable carrier.

In a further embodiment, the invention pertains to a pharmaceutical composition comprising from about 0.1 to about 1500 mg of a compound described herein (e.g., Compound 14), or a salt thereof, and a pharmaceutically acceptable carrier. In a further embodiment, the pharmaceutically acceptable carrier is acceptable for otic, parenteral, intravenous, ophthalmic, nasal, topical, or oral administration.

The language "pharmaceutically acceptable carrier" includes substances capable of being coadministered with a compound described herein (e.g., Compound 14) and which allow the compound to perform its intended function, e.g., treat or prevent a bacterial infection. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-celltilose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances, and the like which do not deleteriously react with the compounds of the present invention.

The compounds described herein can be administered alone or in combination with other known compositions for treating a microbial infection in a subject. The language "in combination with" a known composition is intended to include simultaneous administration of a composition of the present invention and a known composition, administration of a composition of the present invention first, followed by a known composition, and administration of a known composition first, followed by a composition of the present invention. Any therapeutic compositions known in the art for treating a microbial infection can be used in the methods of the present invention. Compounds of the invention may also be used in a combination therapy, e.g., in combination with any other treatment modality.

The compounds and pharmaceutical compositions of the present invention may be administered atone or in combination with pharmaceutically acceptable carriers, diluents or carriers by any of the routes previously mentioned, and the administration may be carried out in single or in multiple doses. The compounds and pharmaceutical compositions of the present invention, administered alone or in combination with pharmaceutically acceptable carriers, diluents or excipients, can be readily administered in a variety of dosage forms such tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of the present invention are present in such dosage forms at concentration levels ranging from about 5.0% by weight to about 70% by weight.

For oral administration, tablets containing various excipients, such as microcrystalline cellulose, sodium citrate, calcium carbonate, dicalcium phosphate, and glycine, may be employed along with various disintegrants, such as starch (and preferably corn, potato or tapioca starch), alginic acid, and certain complex silicates, together with granulation binders like polyvinylpyrrolidone, sucrose, gelatin, and acacia. Additionally, lubricating agents such as magnesium stearate, sodium lauryl sulfate, and talc are often very useful for tableting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin, and various like combinations thereof.

For parenteral administration (including intraperitoneal, subcutaneous, intravenous, intradermal, or intramuscular injection), solutions of the compounds of the present invention in either sesame or peanut oil or in aqueous propylene glycol may be employed. The aqueous solutions should be suitably buffered if necessary and the liquid diluent first rendered isotonic.

These aqueous solutions are suitable for intravenous injection purposes. The oily solutions are suitable for intraarticular, intramuscular and subcutaneous injection purposes. The preparation of all of these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier, e.g., sterile physiological saline or 5% saline dextrose solutions, commonly used with injectables.

For enteral application, particularly suitable are tablets, dragees, or capsules having talc and/or carbohydrate carrier binder or the like, the carrier preferably being lactose and/or corn starch and/or potato starch. A syrup, elixir, or the like can be used wherein a sweetened vehicle is employed. Sustained release compositions can be formulated including those wherein the active component is protected with differentially degradable coatings, e.g., by microencapsulation, multiple coatings, etc.

EXAMPLES

Example 1: Syntheses of Compounds 1-17

Compounds 1-13 were synthesized according to the methods described in WO 2012/173689. Compounds 14-17 were synthesized according to the methods described herein below.

Synthetic Scheme for Compound 14

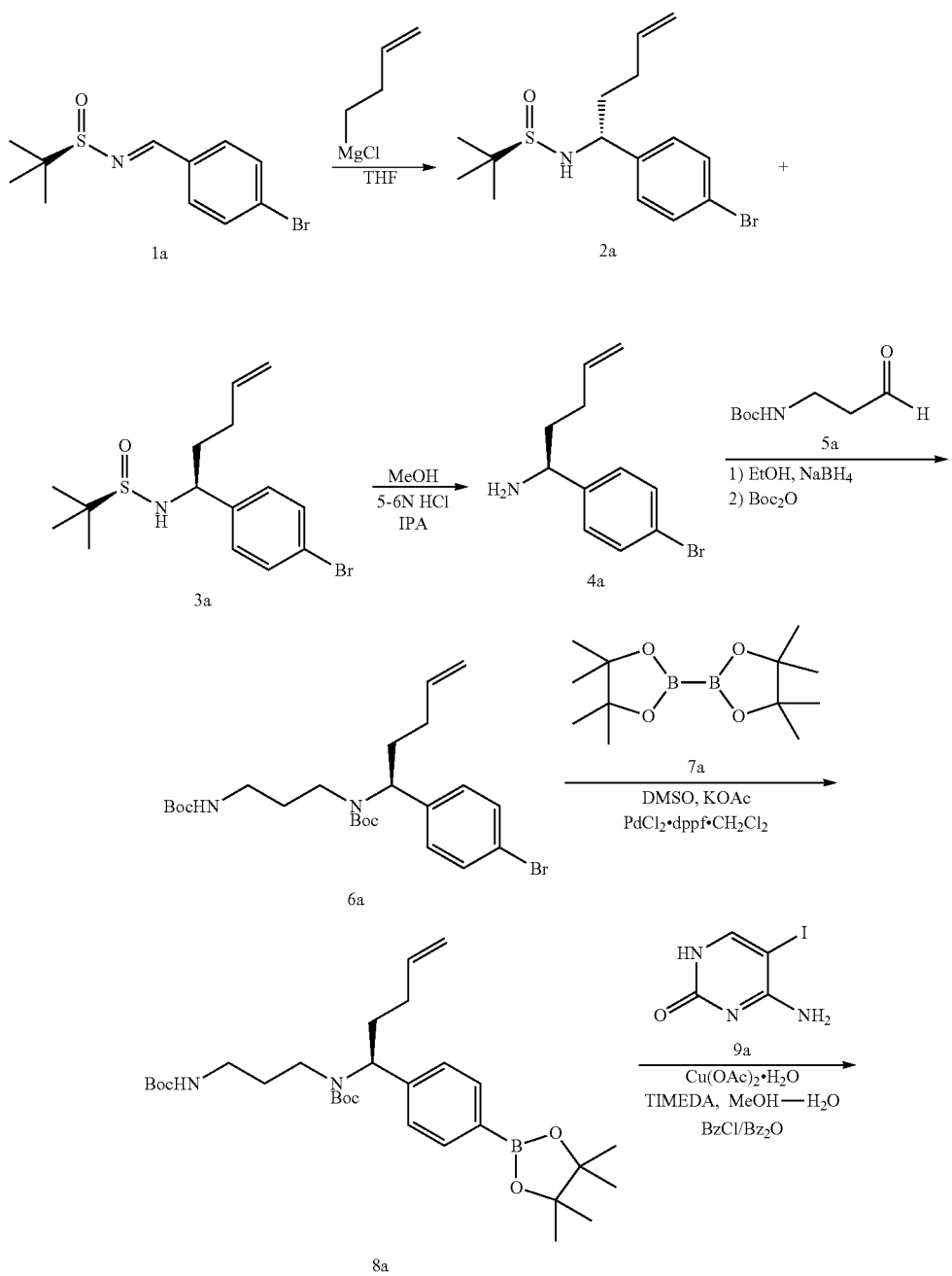

-continued

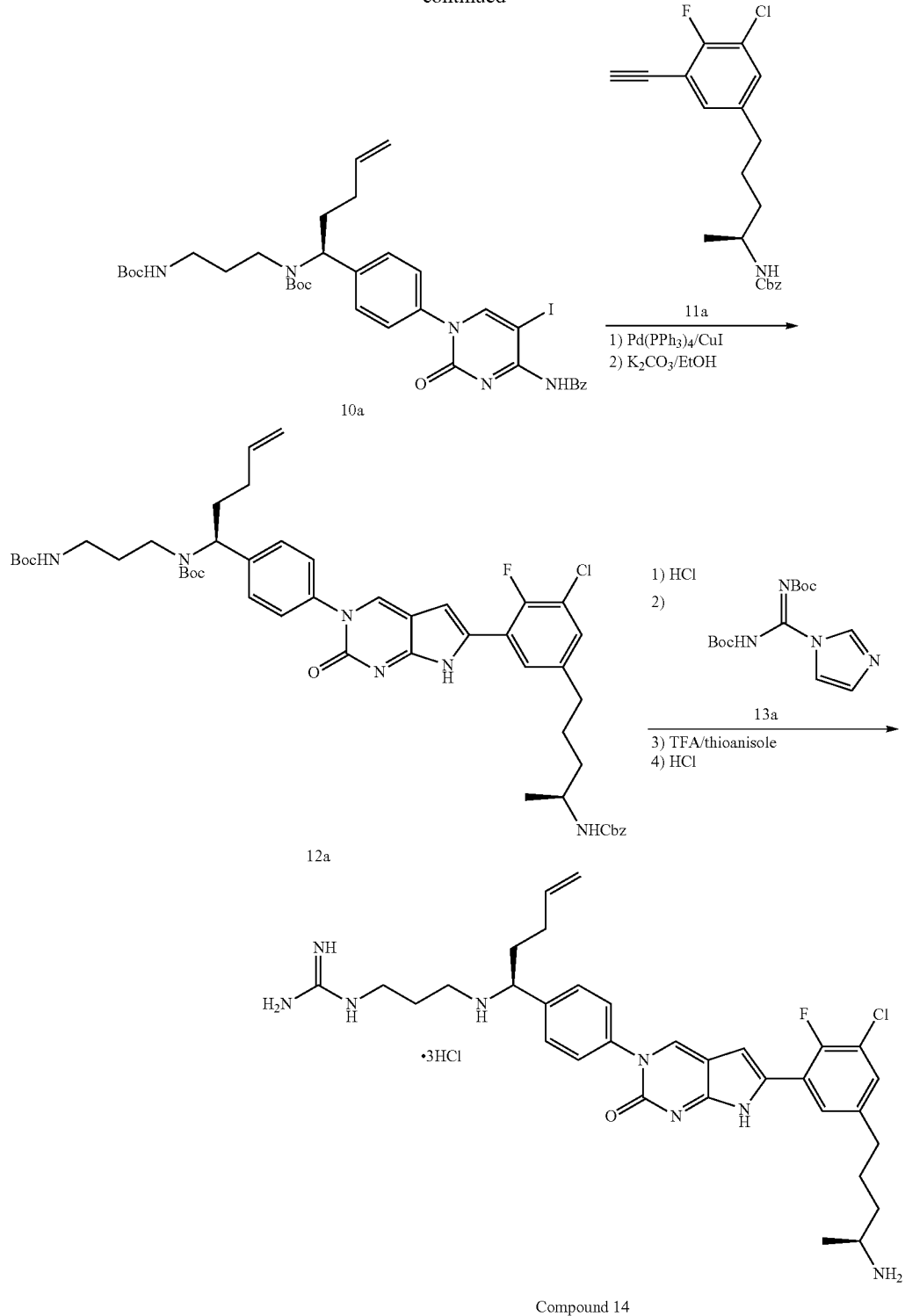

Pyridine para-toluenesulfonate (2.6 g) and magnesium sulfate (124 g) were added to a solution of (R)-(+)-2-methyl-2-propanesulfinamide (25 g) and 4-bromobenzaldehyde (42 g) in dichloromethane (300 mL) and the resulting mixture was stirred overnight at ambient temperature. The mixture was then filtered, concentrated, and purified by flash chromatography over silica gel (5% ethyl acetate in dichloromethane) to afford 48.8 g of compound 1a. A solution of compound 1a (10.1 g) in tetrahydrofuran (THF, 100 mL) was then treated with 3-butenyl magnesium bromide (200 mL, 0.5 M in THF) at −75° C. and the resulting mixture was then slowly warmed up to ambient temperature overnight. The reaction was quenched with saturated ammonium chloride solution, extracted with ethyl acetate (3×100 mL) and the combined organic layers were dried (with anhydrous sodium sulfate), concentrated, and purified by flash chromatography over silica gel (40% ethyl acetate in heptane) to afford 2a and 3a. Treatment of compound 3a (2 g) in methanol (MeOH, 15 mL) with 5-6 N hydrochloric acid (HCl) in isopropanol (IPA, 5 mL) afforded amine 4a (1.2 g) as a hydrochloride salt. Compound 1.4 (ESI, m/z 607.1 [M+H]$^+$) was obtained from compound 4a using a method similar to that described in WO 2012/173689. Synthesis of compound 11a was accomplished as described in WO 2012/173689.

Synthetic Scheme for Compound 15

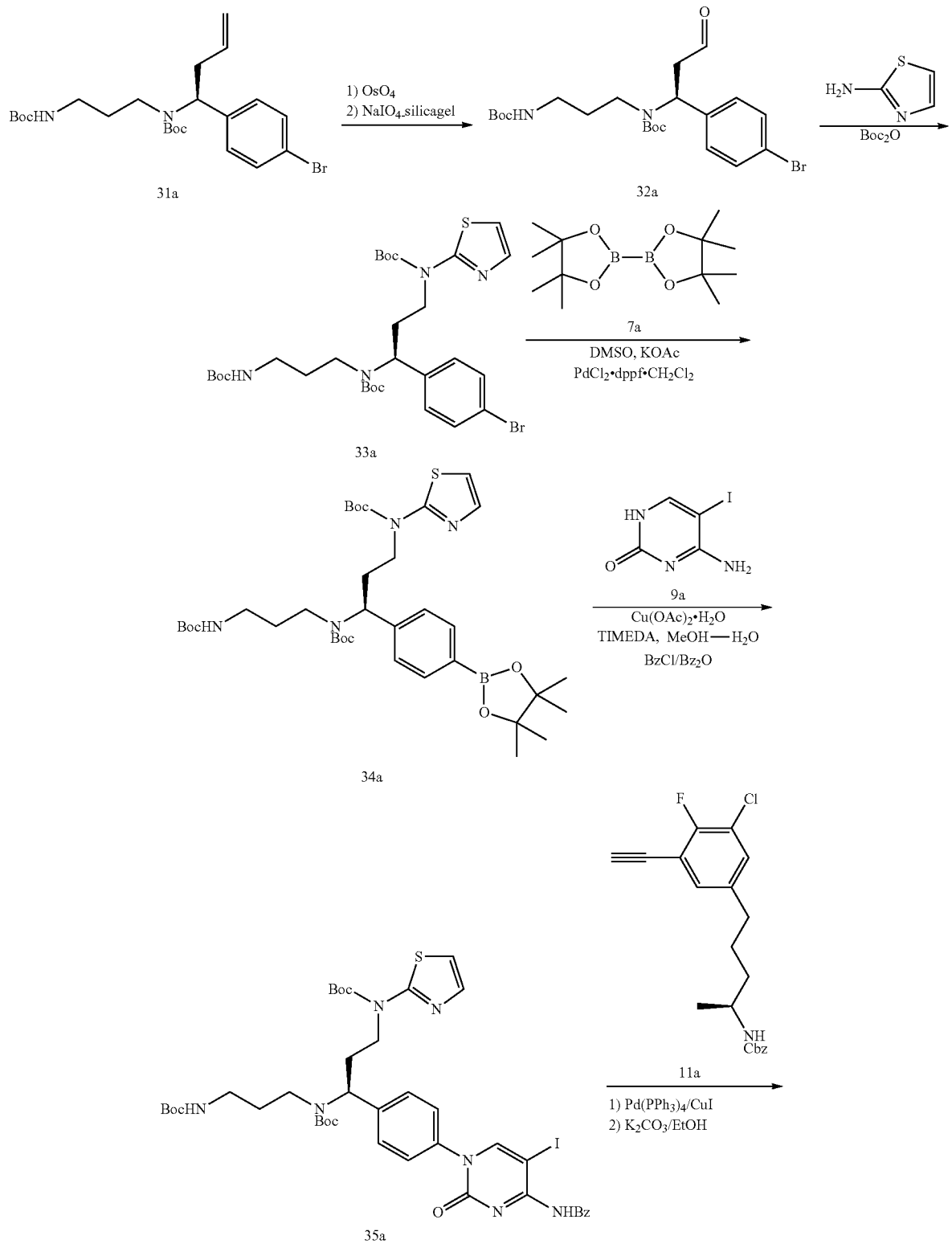

-continued

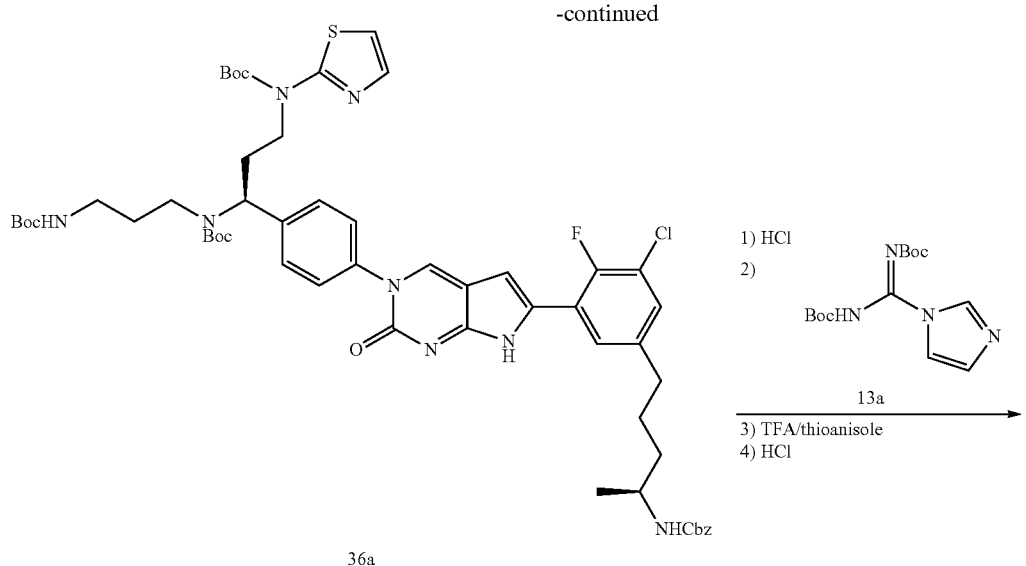

36a

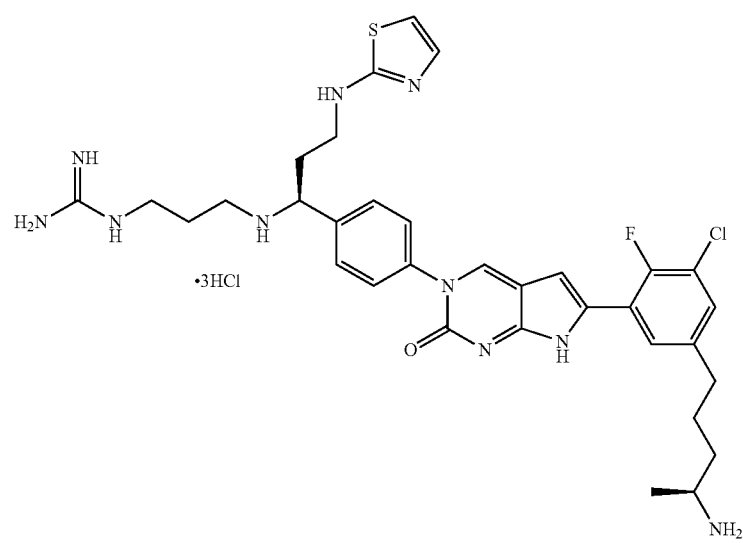

Compound 15

Compound 31a was synthesized using a method similar to that utilized for the synthesis of compound 6a as shown in the synthetic scheme for Compound 14 above 31a was then converted to aldehyde 32a by oxidation of the olefin using osmium tetroxide (OsO$_4$) and sodium periodate-silica gel (NaIO$_4$—SiO$_2$). Reductive amination of aldehyde 32a in the presence of 2-amino thiazole followed by protection of the resulting amine afforded 33a, 33a was then converted to Compound 15 (ESI, m/z 340.1 [M+H]$^{+2}$) using a method similar to that described in WO 2012/173689.

Synthetic Scheme for Compound 16

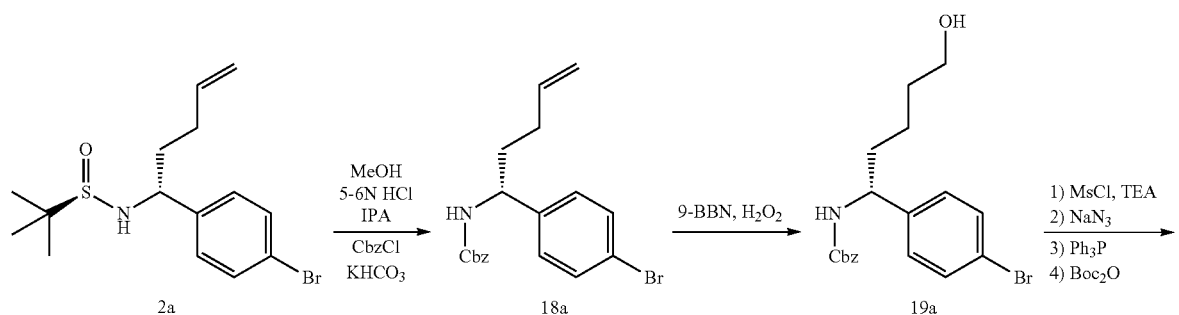

-continued
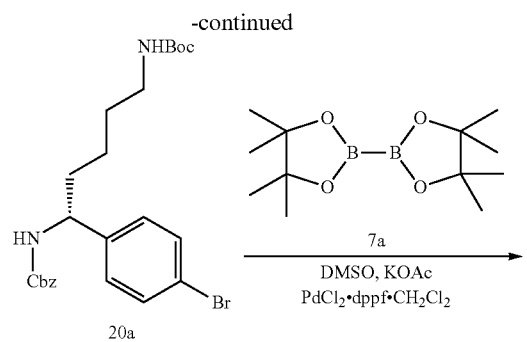
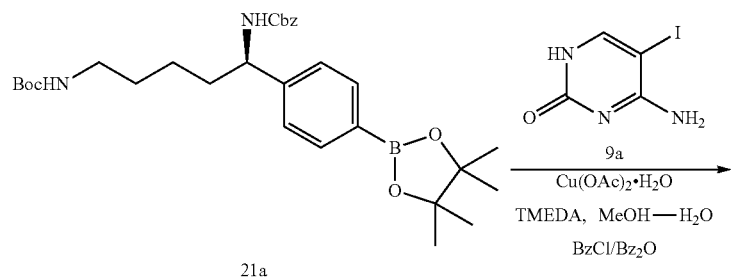
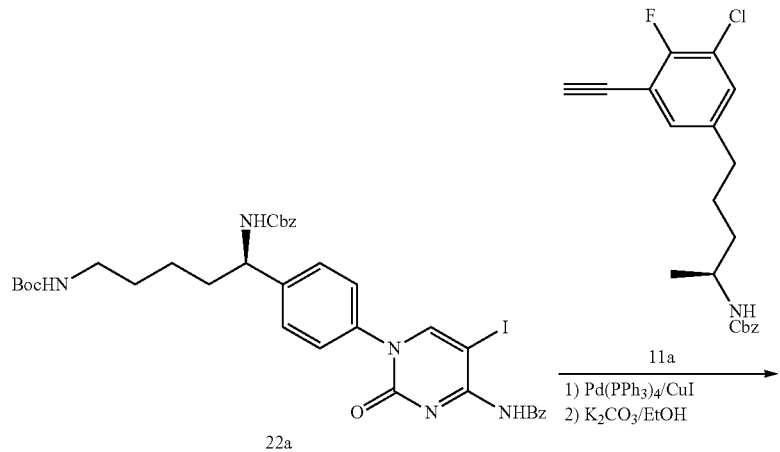
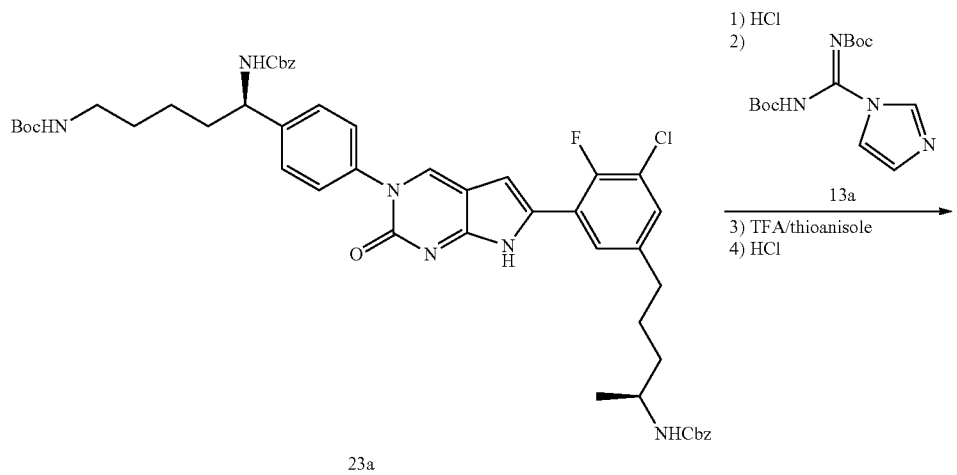

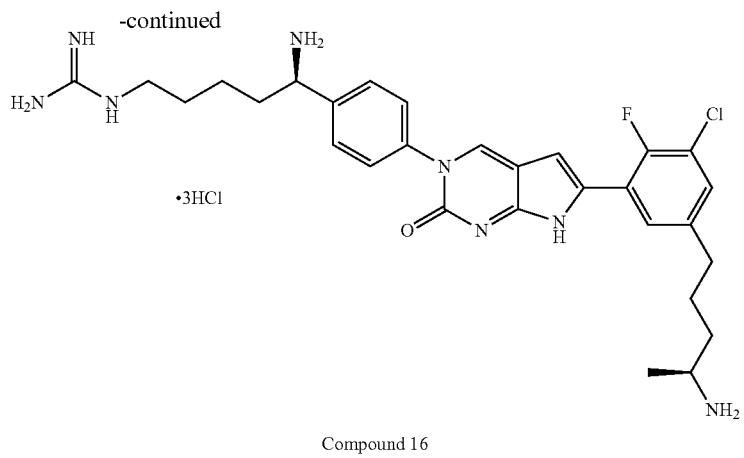

Compound 16

Synthesis of Compound 16 began with treatment of Compound 2a with 5-6 N HCl in isopropanol followed by benzyl chloroformate (Cbz-Cl) and potassium bicarbonate (KHCO$_3$) to afford the protected amine 18a. To a solution of 18a (2.27 g) in TI-IF was added 9-borabicyclo-(3.3.1) nonane (9-BBN, 24.2 ml, 0.5 M in THF) and the resulting mixture was stirred overnight at ambient temperature. The reaction mixture was then quenched with hydrogen peroxide and upon workup afforded 19a (2.3 g). Alcohol 19a was converted to the tBoc protected amine 20a (0.9 g) using standard synthetic protocols as shown in the scheme above. Compound 20a was then converted to Compound 16 (ESI, m/z 567.1 [M+H]$^+$) using a method similar to that described in WO 2012/173689 (See Scheme above).

Synthetic Scheme for Compound 17

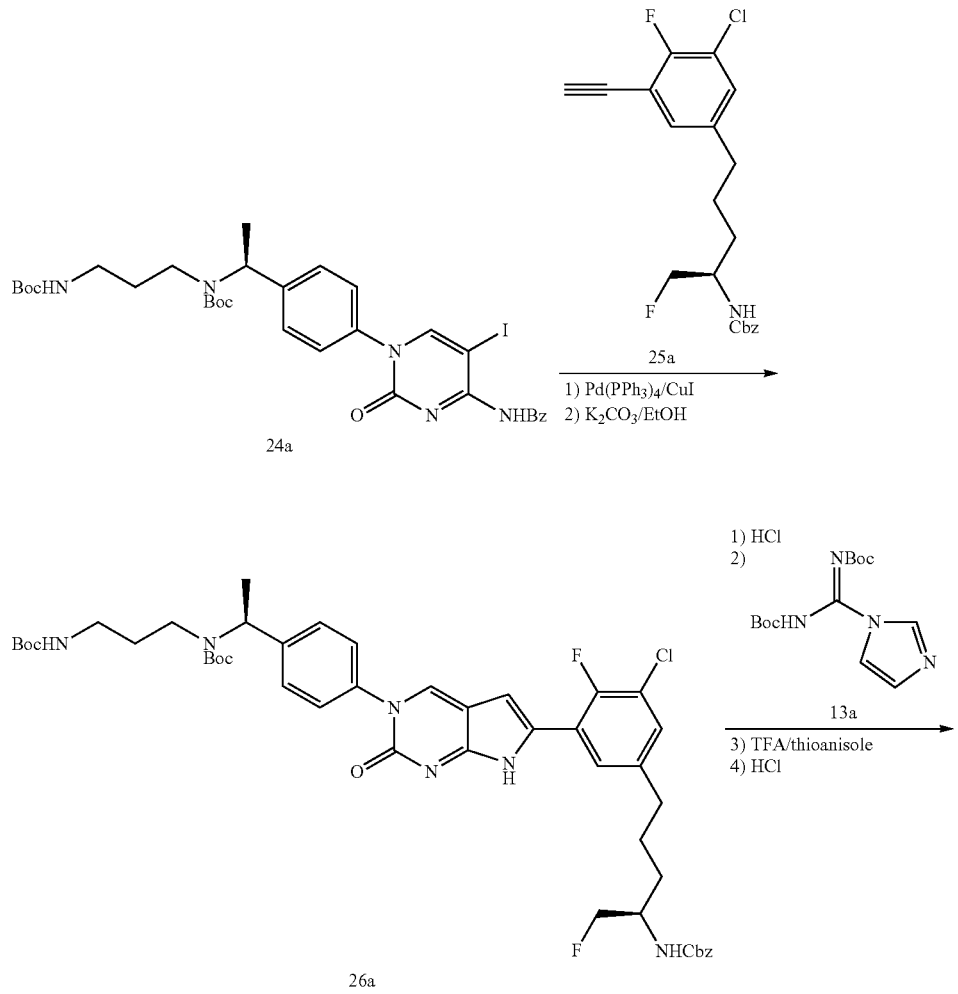

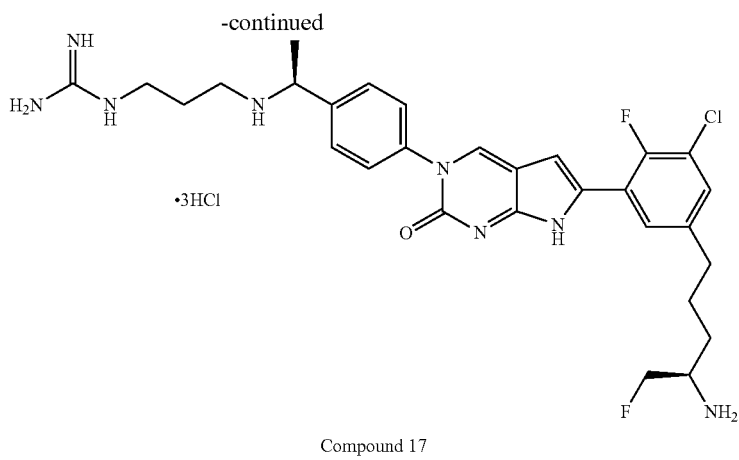

Compound 17

The intermediate 24a (synthesis of which is described in WO 2012/173689) was converted to Compound 17 (ESI, m/z 585.1 [M+H]$^+$) as shown in the scheme above using a method similar to that described in WO 2012/173689. The alkyne derivative 25a was made using the procedure shown in the scheme below.

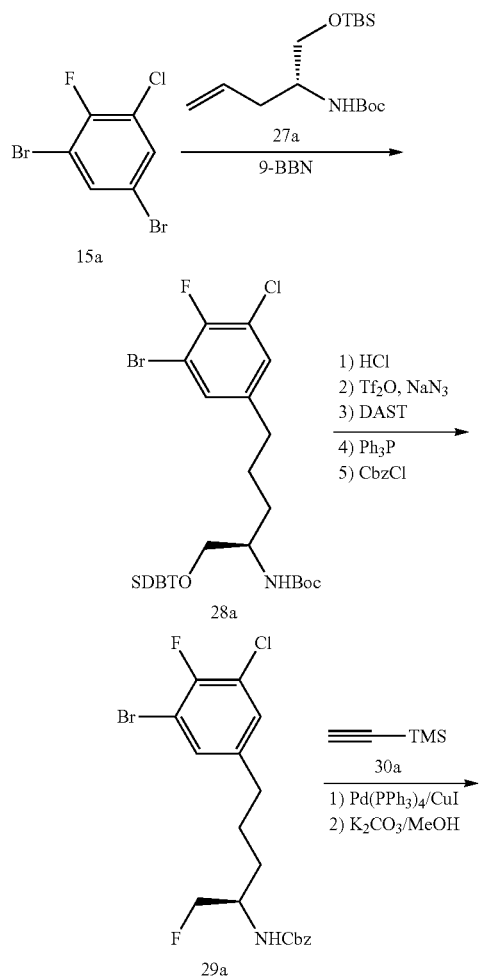

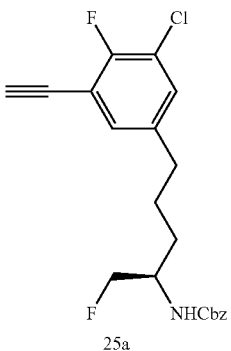

25a

9-Borabicyclo(3.3.1)nonane (9-BBN, 2.1 g) was added to a solution of 27a (4 g) in toluene (15 mL) and tetrahydrofuran (THF, 15 mL) and the resulting mixture was stirred overnight at ambient temperature. The mixture was then concentrated, 15a in toluene (40 mL) and 1N sodium hydroxide (NaOH, 30 mL) was added followed by palladium tetrakis (Pd(PPh$_3$)$_4$) and the resulting mixture was heated to 60° C. for 24 hours. After standard workup and purification procedures, 4.7 g of 28a was obtained. Intermediate 28a was then treated with 6 N HCl to form the corresponding amino alcohol (2.4 g) which was then treated with trifluoromethyl sulfonic anhydride (TfO$_2$) and sodium azide (NaN$_3$) to afford the corresponding azide (2.4 g). The azide (1.7 g) was treated with diethylaminosulfur trifluoride DAST followed by triphenyl phosphine and benzyl chloroformate (Cbz-Cl) to afford pure 29a (0.8 g) after purification by chromatography. Coupling of the polyhalogenated derivative 29a with 30a afforded pure 25a (0.5 g) after work up and purification.

Example 2: Antibacterial Activity of Compounds 1-17

Antibacterial activity (MIC, in μg/mL) of compounds was determined using a microtiter-based liquid assay as described by the Clinical and Laboratory Standards Institute 2008, *Performance Standards for Antimicrobial Susceptibility Testing; Eighteenth Informational Supplement. CLSI Document M*100-*S*18, Clinical and Laboratory Standards institute, 940 West Valley Road, Suite 1400, Wayne, Pa. 19087-1898 USA. The final concentrations of test compounds ranged (typically) from 0.03 μg/mL to 64 μg/mL based on a final well volume of 100 μL after inoculation.

Biodefense Panels

Isolates: Strains represent the United States Army Medical Research Institute for Infectious Diseases' (USAMRIID) standard collection of genetically diverse biothreat isolates that have been routinely used for in vitro MIC profiling. *B. anthracis* isolates included samples from at least 17 genotypes from a wide geographic distribution. *Y. pestis* isolates came from at least 15 different countries and included all 3 known biotypes (orientalis, mediaevalis, and antique) and multiple genotypes. The *F. tularensis* isolates included both A, F, and B biovar types, with "A" being more virulent.

Preparations: Bacterial inoculums were prepared by suspension of colonies into cation-adjusted Mueller-Hinton broth (cAmHB) from 18 to 24 hours for *B. anthracis, B. pseudomallei, B. mallei* plates; or 42 to 48 hours for *F. tularensis* and *Y. pestis* plates that were incubated at 35° C. Sheep Blood agar (SBA) plates were used for *B. anthracis* and *Y. pestis*; chocolate agar plates for *F. tularensis*; and Trypticase Soy agar (TSA) plates for *B. pseudomallei* and *B. mallei*. Suspended cultures were diluted with CAMHB to a bacterial cell density of $10^5$ CFU/mL using a 0.5 McFarland standard. To each well of the 96-well plate, 50 μL of the adjusted dilution solution was added for a final inoculum of approximately $5.0 \times 10^4$ CFU/well.

Experimental Protocol: Minimum inhibitory concentrations (MICs) were determined by the microdilution method in 96-well plates according to Clinical and Laboratory Standards Institute (CLSI). Antibiotics were serially diluted twofold in 50 μL of CAMHB. For all steps with *F. tularensis*, CAMHB inoculum broth was supplemented with 2% Isovitalex (Becton Dickinson). The antibiotic ranges were based on a final well volume of 100 μL after inoculation. Plates were incubated at 35° C. MICs were determined visually at 16 to 20 hours or at 48 hours (*F. tularensis* and *Y. pestis*).

Quality Control: Quality control of the testing procedure was established by using *E. coli* ATCC 25922, *P. aeruginosa* ATCC 27853, and *S. aureus* ATCC 29213. Inoculums were prepared as described above from 18 to 24 hours on SBA plates. Ciprofloxacin, ceftazidime, or azithromycin were tested in each run and their MICs were compared to historical USAMRIID data as QC (data not shown).

Drugs and Materials: Compounds were provided as pure powders. Working stocks were made in 100% DMSO and frozen as 50 μL at stocks at −70° C. These 50 μL at stocks were brought to 1 mL in CAMHB prior to final dilution in the 96-well plates. Ciprofloxacin, ceftazidime, and azithromycin were all purchased from USP, made into 5 mg/mL stocks according to the CLSI M100-S18 Table 4 guidelines, and stored at −70° C. until use.

Computational Methods: Molecular properties were computed using QikProp version 3.0.001. Data analysis was performed using IMP, version 8.0.

The MIC results of test compounds are shown in Tables 1 and 3 below. Table 2 includes comparative MIC data from known antibiotics against the ESKAPE (*Enterococcus faecium, Staphylococcus aureus, Klebsiella pneumoniae, Acinetobacter baumannii, Pseudomonas aeruginosa*, and *Enterobacter* species) pathogens. The data in Table 1 demonstrate the potent and broad antimicrobial activity of Compounds 1-17 against the ESKAPE pathogens. The data in Table 3 demonstrate that Compounds 1-17 are broadly active against the biodefense bacteria *B. anthracis, Y. pestis, F. tularensis, B. mallei* and, in the most potent examples, *B. pseudomallei*.

TABLE 1

| | MICs (μg/mL) of Compounds Tested | | | | | | | | | | | | | | | | |
|---|---|---|---|---|---|---|---|---|---|---|---|---|---|---|---|---|---|
| Bacterial Strains | 1 | 2 | 3 | 4 | 5 | 6 | 7 | 8 | 9 | 10 | 11 | 12 | 13 | 14 | 15 | 16 | 17 |
| *E. coli* ATCC25922 | 0.125 | 0.125 | 0.25 | 0.125 | 0.125 | 0.5 | 0.5 | 0.5 | 0.25 | 0.25 | 0.25 | 0.125 | 0.25 | 0.5 | 0.5 | 0.125 | 0.25 |
| *E coli* ATCC25922 + 50% HS | 0.125 | 0.25 | 0.5 | 0.5 | 0.25 | 0.25 | 1 | 2 | 0.5 | 0.25 | 0.5 | 0.5 | 0.25 | 2 | 0.5 | 0.125 | 0.5 |
| *E. coli* 1705878 | 1 | 1 | 0.5 | 0.5 | 2 | 1 | 1 | 1 | 0.5 | 0.5 | 0.5 | 0.25 | 0.25 | 1 | 2 | 0.5 | 2 |
| *E. coli* MG1655 parent | 0.5 | 0.25 | 0.5 | 0.25 | 0.5 | 0.25 | 0.5 | 0.25 | 0.25 | 0.25 | 0.25 | 0.25 | 0.25 | 1 | 1 | 0.25 | 1 |
| *E. coli* CAG12184 TolC | 0.06 | 0.125 | 0.25 | 0.25 | 0.06 | 0.25 | 0.5 | 0.25 | 0.25 | 0.25 | 0.25 | 0.125 | 0.25 | 0.5 | 0.25 | 0.06 | 0.125 |
| *S. pneumoniae* 02J1175 Mef(A) | 0.25 | 0.125 | 0.25 | 0.5 | 0.125 | 0.25 | 0.25 | 0.5 | 0.25 | 0.25 | 2 | 0.125 | 0.25 | 0.5 | 0.25 | 0.25 | 0.125 |
| *S. aureus* 11540 MRSA | 0.125 | 0.25 | 0.25 | 0.25 | 0.125 | 0.25 | 0.5 | 0.25 | 0.25 | 0.25 | 0.5 | 0.125 | 0.25 | 0.5 | 0.5 | 0.25 | 0.25 |
| *K. pneumoniae* 1705949 | 2 | 0.5 | 1 | 1 | 0.5 | 2 | 1 | 2 | 0.5 | 0.5 | 8 | 0.25 | 0.5 | 1 | 1 | 2 | 1 |
| *K. pneumoniae* 1705966 | 0.25 | 0.25 | 0.25 | 0.25 | 0.125 | 0.5 | 0.5 | 1 | 0.25 | 0.25 | 1 | 0.125 | 0.25 | 0.5 | 0.25 | 0.25 | 0.125 |
| *A. baumannii* 1705936 | 4 | 4 | 2 | 4 | 2 | 4 | 4 | 1 | 0.5 | 2 | 1 | 2 | 4 | 0.5 | 1 | 2 | 1 |
| *A. baumannii* 1705943 | 0.25 | 0.25 | 0.25 | 0.25 | 0.25 | 0.25 | 0.5 | 0.5 | 0.25 | 0.25 | 0.25 | 0.25 | 0.25 | 0.5 | 0.5 | 0.125 | 0.25 |
| *P. aeruginosa* ATCC27853 | 4 | 4 | 8 | 4 | 4 | 8 | 8 | 4 | 2 | 4 | 4 | 4 | 2 | 4 | 8 | 4 | 8 |
| *P. aeruginosa* 1705886 | 2 | 2 | 4 | 2 | 4 | 4 | 4 | 4 | 2 | 2 | 4 | 2 | 2 | 2 | 4 | 4 | 4 |
| *P. aeruginosa* 1705904 | 8 | 8 | 8 | 4 | 8 | 8 | | 4 | 4 | 4 | 8 | 4 | 4 | 4 | 8 | 8 | 8 |
| *E. faecium* A6349 VanA + LNZ-R | 4 | 2 | 2 | 4 | 1 | 4 | 2 | 4 | 0.5 | 0.5 | 4 | 0.5 | 0.5 | 1 | 2 | 2 | 0.5 |

TABLE 2

| Bacterial Strains | Ciprofloxacin MICs (μg/mL) | Tigecycline MICs (μg/mL) | Tobramycin MICs (μg/mL) |
|---|---|---|---|
| *E. coli* ATCC25922 | 0.0078125 | 0.125 | 1 |
| *E. coli* ATCC25922 + 50% HS | 0.0078125 | 0.25 | 1 |

TABLE 2-continued

| Bacterial Strains | Ciprofloxacin MICs (µg/mL) | Tigecycline MICs (µg/mL) | Tobramycin MICs (µg/mL) |
|---|---|---|---|
| E. coli 1705878 | >128 | 0.5 | 64 |
| E. coli MG1655 parent | 0.0078125 | 0.25 | 1 |
| E. coli CAG12184 TolC | 0.00390625 | 0.125 | 1 |
| S. pneumoniae 02J1175 Mef(A) | 1 | <=0.06 | 16 |
| S. aureus 11540 MRSA | 128 | 0.25 | 0.5 |
| K. pneumoniae 1705949 | >128 | 1 | >128 |
| K. pneumoniae 1705966 | 0.0078125 | 0.5 | <=0.25 |
| A. baumannii 1705936 | >128 | 2 | 8 |
| A. baumannii 1705943 | 0.25 | 0.125 | <=0.25 |
| P. aeruginosa ATCC27853 | <=0.25 | 8 | 0.5 |
| P. aeruginosa 1705886 | 0.06 | 8 | 0.5 |
| P. aeruginosa 1705904 | >128 | >32 | 128 |
| E. faecium A6349 VanA + LNZ-R | >128 | <=0.06 | >128 |

TABLE 3

| | B. anthracis | | | Y. pestis | | | B. mallei | | |
|---|---|---|---|---|---|---|---|---|---|
| Cpd | Range | MIC$_{50}$ | MIC$_{90}$ | Range | MIC$_{50}$ | MIC$_{90}$ | Range | MIC$_{50}$ | MIC$_{90}$ |
| 1 | ≤0.03-0.25 | 0.12 | 0.25 | ≤0.03-0.5 | 0.12 | 0.25 | ≤0.03-0.25 | ≤0.03 | 0.06 |
| 2 | ≤0.03-1 | 0.12 | 0.12 | ≤0.03-0.25 | 0.12 | 0.25 | ≤0.03-0.25 | ≤0.03 | 0.06 |
| 3 | ≤0.03-2 | 0.25 | 0.25 | ≤0.03-1 | 0.25 | 0.5 | ≤0.03-0.5 | 0.06 | 0.12 |
| 4 | 0.06-4 | 0.5 | 0.5 | ≤0.03-0.5 | 0.25 | 0.25 | ≤0.03-0.5 | ≤0.03 | 0.12 |
| 5 | ≤0.03-2 | 0.12 | 0.12 | ≤0.03-2 | 0.25 | 0.5 | ≤0.03-0.5 | 0.06 | 0.25 |
| 6 | 0.06-1 | 0.5 | 0.5 | ≤0.03->16 | 0.25 | >16 | ≤0.03-0.5 | ≤0.03 | 0.12 |
| 7 | ≤0.03-0.5 | 0.12 | 0.25 | 0.06-1 | 0.25 | 0.5 | ≤0.03-0.5 | 0.06 | 0.12 |
| 8 | 0.12-1 | 0.5 | 1 | ≤0.03-0.5 | 0.12 | 0.25 | ≤0.03-0.25 | ≤0.03 | 0.12 |
| 8 | ≤0.03-0.25 | 0.12 | 0.25 | ≤0.03-0.25 | 0.06 | 0.12 | ≤0.03-0.25 | ≤0.03 | 0.12 |
| 10 | ≤0.03-0.25 | 0.12 | 0.25 | ≤0.03-0.25 | ≤0.03 | 0.06 | ≤0.03-0.25 | ≤0.03 | 0.12 |
| 11 | 0.12-0.5 | 0.25 | 0.5 | ≤0.03-0.5 | ≤0.03 | 0.12 | ≤0.03-0.25 | ≤0.03 | 0.12 |
| 12 | ≤0.03-0.25 | 0.06 | 0.12 | ≤0.03-0.5 | 0.12 | 0.25 | ≤0.03-0.25 | ≤0.03 | 0.12 |
| 13 | ≤0.03-0.12 | ≤0.03 | 0.12 | ≤0.03-0.25 | 0.06 | 0.12 | ≤0.03-0.25 | ≤0.03 | 0.06 |
| 14 | ≤0.03-0.5 | 0.25 | 0.25 | ≤0.03-0.5 | 0.12 | 0.5 | ≤0.03-0.5 | ≤0.03 | 0.25 |
| 15 | ≤0.03-0.25 | 0.12 | 0.12 | 0.06-1 | 0.5 | 1 | ≤0.03-0.5 | 0.06 | 0.25 |
| 16 | ≤0.03-0.12 | ≤0.03 | 0.06 | ≤0.03-0.5 | 0.12 | 0.25 | ≤0.03-0.06 | ≤0.03 | 0.06 |
| 17 | ≤0.03-0.5 | 0.25 | 0.25 | ≤0.03-0.5 | 0.25 | 0.5 | ≤0.03-0.25 | 0.06 | 0.25 |
| Ciprofloxacin | 0.015-0.25 | 0.03 | 0.03 | ≤0.004-0.5 | 0.015 | 0.03 | n.d. | n.d. | n.d. |
| Azithromycin | n.d. | n.d. | n.d. | n.d. | n.d. | n.d. | 0.12-1 | 0.5 | 1 |
| Ceftazidime | n.d. | n.d. | n.d. | n.d. | n.d. | n.d. | n.d. | n.d. | n.d. |

| | F. tularensis | | | B. pseudomallei | | |
|---|---|---|---|---|---|---|
| Cpd | Range | MIC$_{50}$ | MIC$_{90}$ | Range | MIC$_{50}$ | MIC$_{90}$ |
| 1 | ≤0.03-0.5 | ≤0.03 | ≤0.03 | 0.5-16 | 4 | 4 |
| 2 | ≤0.03-0.25 | ≤0.03 | ≤0.03 | 0.5-8 | 2 | 4 |
| 3 | ≤0.03-1 | ≤0.03 | 0.12 | 0.5-8 | 2 | 4 |
| 4 | ≤0.03-1 | ≤0.03 | ≤0.03 | 0.5-8 | 2 | 4 |
| 5 | ≤0.03-0.25 | ≤0.03 | ≤0.03 | 1-≤64 | 16 | 16 |
| 6 | ≤0.03-1 | ≤0.03 | 0.06 | 1-32 | 8 | 16 |
| 7 | ≤0.03-0.5 | 0.06 | 0.12 | 1-8 | 2 | 4 |
| 8 | ≤0.03-2 | 0.06 | 0.25 | 1-8 | 4 | 8 |
| 8 | ≤0.03-4 | 0.06 | 0.12 | 0.25-8 | 1 | 2 |
| 10 | ≤0.03-4 | ≤0.03 | 0.06 | 0.25-8 | 1 | 2 |
| 11 | ≤0.03-4 | 0.06 | 0.25 | 0.25-8 | 1 | 4 |
| 12 | ≤0.03-1 | ≤0.03 | ≤0.03 | 0.5-16 | 4 | 8 |
| 13 | ≤0.03-0.5 | ≤0.03 | ≤0.03 | 0.5-16 | 4 | 8 |
| 14 | ≤0.03-2 | 0.06 | 0.25 | 0.25-8 | 2 | 4 |
| 15 | ≤0.03-2 | 0.06 | 0.25 | 4-32 | 8 | 16 |
| 16 | ≤0.03-1 | ≤0.03 | 0.12 | 2-16 | 4 | 8 |
| 17 | ≤0.03-1 | ≤0.03 | 0.12 | 1-16 | 8 | 16 |
| Ciprofloxacin | 0.008-1 | 0.03 | 0.06 | n.d. | n.d. | n.d. |
| Azithromycin | n.d. | n.d. | n.d. | n.d. | n.d. | n.d. |
| Ceftazidime | n.d. | n.d. | n.d. | 1-64 | 2 | 4 |

Note that the MICs values in Table 3 are in the unit of µg/mL, and N strains = 30

An analysis of the effects driving the antibacterial activity, with emphasis on the activity against B. pseudomallei, was undertaken. It was found that the activity against B. pseudomallei correlates with the activity against P. aeruginosa and with key shared molecular features, including a display of hydrophobic surface area.

The dataset above was combined with sixteen pyrrolocytosine compounds from an earlier surveillance study, such as those described in Hershfield, J. et al. *Antibacterial Activity of Novel RX*-04 *Compounds Against Biodefense Pathogens*. Poster F-1522, $52^{nd}$ ICAAC, 2012. Molecular properties were computed for each compound, MICs, expressed as log base 2, were included for the MDR strains from the therapeutic panel, including *E. coli* 1705878, *K. pneumoniae* 1705949, *P. aeruginosa* 1705904, and *A. baumannii* 1705936.

As shown in the half-normal plot in FIG. 1, a sensitivity analysis revealed two main features showing the greatest likelihood of a significant effect (activity against the *P. aeruginosa* 1705904 MDR strain and increased hydrophobic solvent-accessible surface area, FOSA), with individual p-values of 0.003 and 0.0043, and two features showing some discrimination, with p-values of 0.0310 and 0.0833. It was shown in the earlier study that enhanced activity against the MDR *P. aeruginosa* strain best correlated with activity against *B. pseudomallei*, and that this was driven by a narrowing of the efflux window. Alone, it describes 40% of the data in this broader dataset. When greater hydrophobicity is included, more than 60% of the data are well-explained. Layering-on the higher-order effect (activity against MDR *P. aeruginosa* and aromatic solvent-accessible surface area, PISA), nearly 70% of the data are explained. A power analysis, using $\alpha=0.05$, indicated that the chances of detecting a significant effect for the three features are >99%, 87% and 63%, respectively, as shown in Table 4 below.

TABLE 4

| 3-Component Model Statistics | |
| --- | --- |
| $r^2$ | 0.67 |
| $r^2$ adjusted | 0.63 |
| RMS | 0.63 |
| MDR Pseudo | 0.9954 |
| FOSA | 0.8712 |
| MDR Pseudo*PISA | 0.6343 |

INCORPORATION BY REFERENCE

The entire disclosure of each of the patent documents and scientific articles referred herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is Elms indicated by the appended claims rather than by the foregoing description, and all changes that come within the meaning and range of equivalency of the claims are intended to be embraced therein.

What is claimed is:

1. A method of treating a microbial infection in a subject, comprising administering to the subject an effective amount of a compound selected from Compounds 1-17:

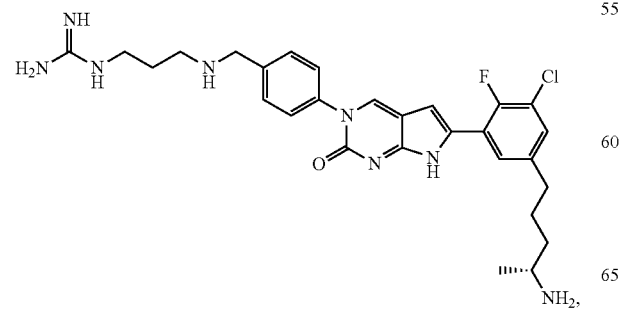
(1)

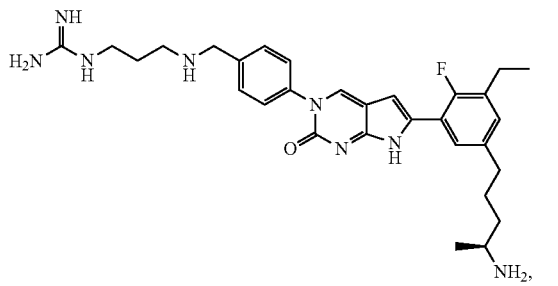
(2)

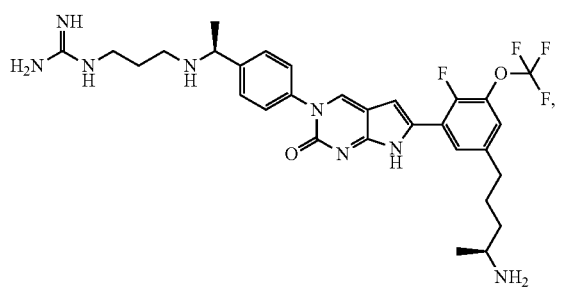
(3)

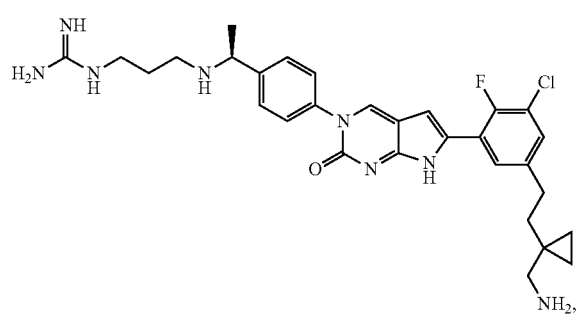
(4)

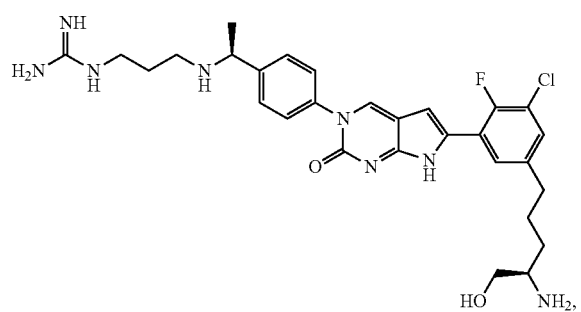
(5)

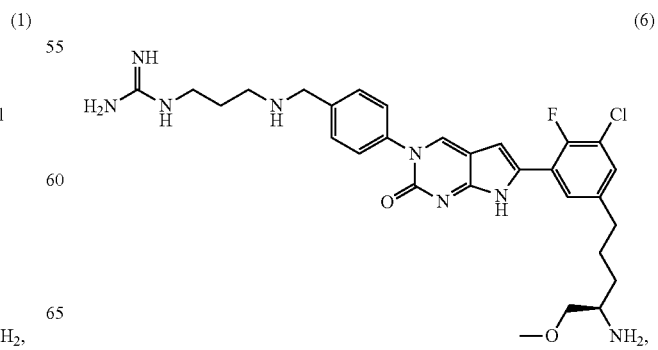
(6)

-continued
(7)
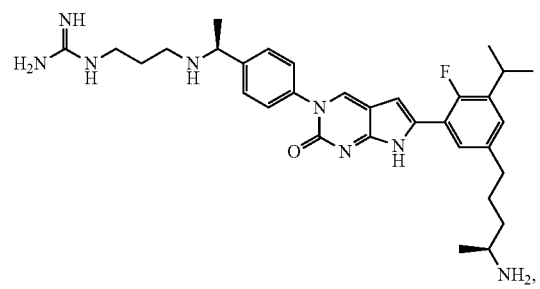
(8)
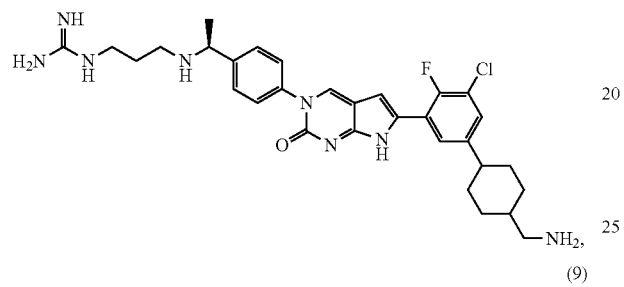
(9)
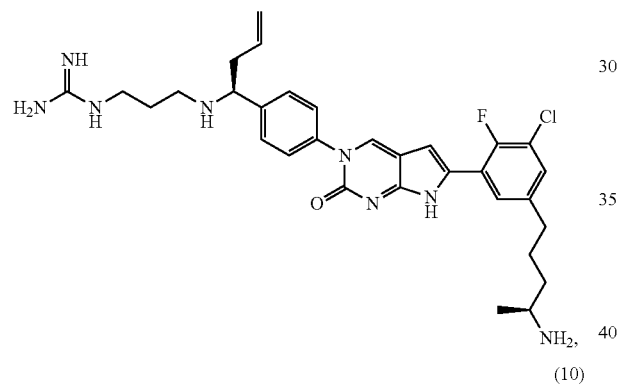
(10)
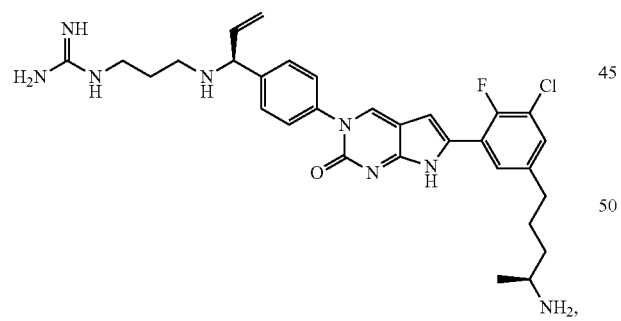
(11)
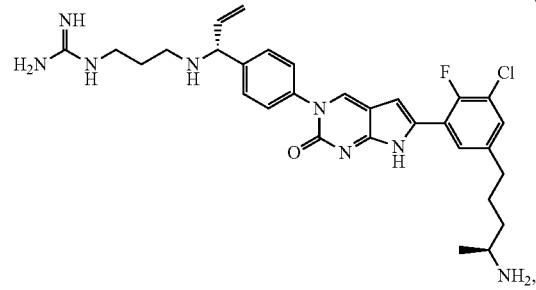
-continued
(12)
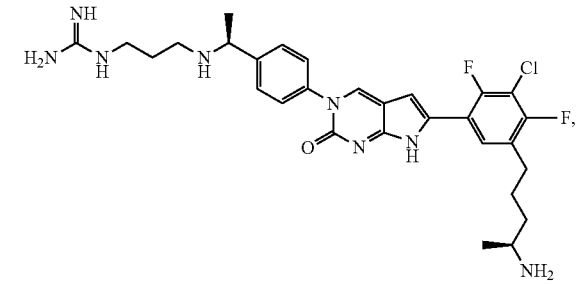
(13)
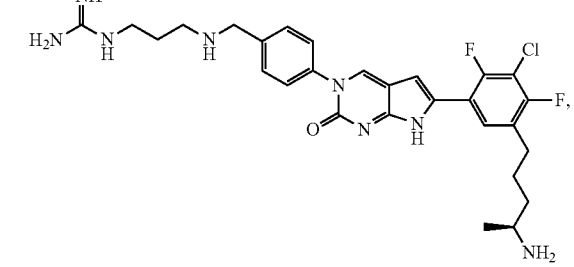
(14)
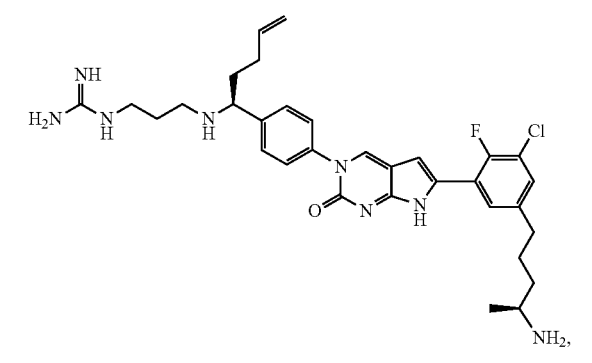
(15)
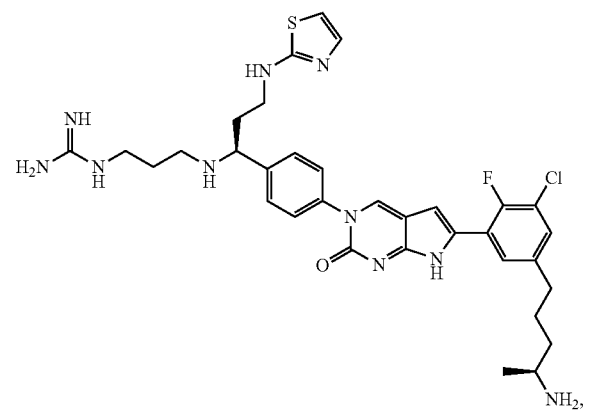

-continued

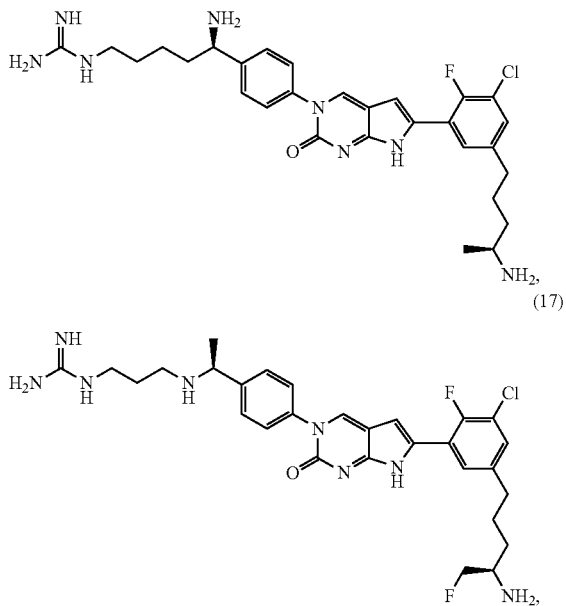

and stereoisomers, tautomers, and salts thereof,
wherein the infection is caused by or involves one or more microorganisms which are capable of being used as biological weapons, or the infection is caused by or involves one or more microorganisms which are extremely-drug resistant Gram-positive or Gram-negative pathogens.

2. The method of claim 1, wherein the compound is selected from the group consisting of Compounds 14-17, stereoisomers, tautomers, and salts thereof.

3. The method of claim 1, wherein the one or more microorganisms are selected from the group consisting of biodefense category A pathogens *Bacillus anthracis* (anthrax), *Yersinia pestis* (plague), and *Fracisella tularensis* (tularemia).

4. The method of claim 1, wherein the one or more microorganisms are selected from the group consisting of biodefense category B pathogens *Burkholderia pseudomallei, Coxiella burnetii* (Q fever), *Brucella* species (brucellosis), *Burkhoderia mallei* (glanders), *Chlamydia psittaci* (Psittacosis), Typhus fever (*Rickettsia* prow azekii), Diarrheagenic *E. coli*, Pathogenic Vibrios, *Shigella* species, *Salmonella, Listeria monocytogenes, Campylobacter jejuni*, and *Yersinia enterocolitica*.

5. The method of claim 1, wherein the one or more microorganisms are selected from *Bacillus anthracis, Franciscella tularensis, Yersinia pestis, Burkholderia mallei*, and *Burkholderia pseudomallei*.

6. The method of claim 5, wherein the one or more microorganisms are *Burkholderia pseudomallei*.

7. The method of claim 1, wherein the one or more microorganisms are extremely-drug resistant Gram-positive or Gram-negative pathogens.

8. The method of claim 1, wherein the compound is selected from the group consisting of Compounds 1-13, stereoisomers, tautomers, and salts thereof, and the one or more microorganisms are selected from *Burkholderia mallei* and *Burkholderia pseudomallei*.

9. The method of claim 1, wherein the salts are pharmaceutically acceptable salts.

10. The method of claim 1, wherein the effective amount is from about 0.1 mg to about 1500 mg, wherein about means within 15% more or less of the specified value.

11. The method of claim 1, wherein the compound is administered otically, ophthalmically, nasally, orally, parenterally, topically, or intravenously.

* * * * *